US009259440B2

(12) United States Patent
Bisgaard-Frantzen

(10) Patent No.: US 9,259,440 B2
(45) Date of Patent: Feb. 16, 2016

(54) METHODS FOR PASSIVE IMMUNIZATION

(71) Applicant: MULTIMERICS ApS, Aalborg Øst (DK)

(72) Inventor: Kirsten Bisgaard-Frantzen, Birkerød (DK)

(73) Assignee: MULTIMERICS ApS, Aalborg Øst (DK)

( * ) Notice: Subject to any disclaimer, the term of this patent is extended or adjusted under 35 U.S.C. 154(b) by 123 days.

(21) Appl. No.: 13/930,941

(22) Filed: Jun. 28, 2013

(65) Prior Publication Data

US 2013/0287780 A1   Oct. 31, 2013

Related U.S. Application Data

(63) Continuation of application No. 12/863,745, filed as application No. PCT/DK2009/050016 on Jan. 22, 2009, now Pat. No. 8,475,789.

(30) Foreign Application Priority Data

Jan. 22, 2008   (DK) .......................... PA 2008 00078

(51) Int. Cl.
| | | |
|---|---|---|
| A61K 35/20 | (2006.01) | |
| A23C 3/08 | (2006.01) | |
| A23C 9/20 | (2006.01) | |
| A23K 1/16 | (2006.01) | |
| A23K 1/18 | (2006.01) | |
| A23L 1/29 | (2006.01) | |
| A23L 1/305 | (2006.01) | |
| A23L 3/3472 | (2006.01) | |
| C07K 16/04 | (2006.01) | |
| A61L 2/00 | (2006.01) | |

(52) U.S. Cl.
CPC . *A61K 35/20* (2013.01); *A23C 3/08* (2013.01); *A23C 9/206* (2013.01); *A23K 1/1631* (2013.01); *A23K 1/1646* (2013.01); *A23K 1/1893* (2013.01); *A23L 1/296* (2013.01); *A23L 1/3056* (2013.01); *A23L 3/3472* (2013.01); *C07K 16/04* (2013.01); *A61L 2/0082* (2013.01)

(58) Field of Classification Search
None
See application file for complete search history.

(56) References Cited

U.S. PATENT DOCUMENTS

| | | |
|---|---|---|
| 3,911,108 A | 10/1975 | Singh |
| 4,644,056 A | 2/1987 | Kothe et al. |
| 4,784,850 A | 11/1988 | Abraham |
| 5,147,548 A | 9/1992 | Hies et al. |
| 5,198,213 A | 3/1993 | Stott et al. |
| 5,256,437 A | 10/1993 | Degen et al. |
| 5,670,196 A | 9/1997 | Gregory |
| 5,683,733 A | 11/1997 | Krabsen et al. |
| 5,707,678 A | 1/1998 | Gregory |
| 6,172,040 B1 | 1/2001 | Naidu |
| 2002/0004587 A1* | 1/2002 | Miller et al. ................ 530/388.8 |
| 2003/0012779 A1 | 1/2003 | Grieb et al. |
| 2003/0093832 A1* | 5/2003 | Szarka et al. ................. 800/281 |
| 2003/0138440 A1* | 7/2003 | Fang et al. .................. 424/185.1 |
| 2004/0185040 A1 | 9/2004 | Garcia-Martinez et al. |
| 2005/0191289 A1 | 9/2005 | Wyss et al. |
| 2005/0241023 A1* | 10/2005 | Hein et al. ..................... 800/288 |
| 2007/0264264 A1* | 11/2007 | Evans et al. ................ 424/157.1 |
| 2008/0299121 A1* | 12/2008 | Fang .......................... 424/136.1 |
| 2010/0166734 A1* | 7/2010 | Dolk .......................... 424/130.1 |
| 2011/0223645 A1* | 9/2011 | Hansen et al. ................ 435/188 |

FOREIGN PATENT DOCUMENTS

| | | |
|---|---|---|
| CA | 1 210 329 A1 | 8/1986 |
| EP | 0 269 405 A2 | 6/1988 |
| EP | 0 417 821 A1 | 3/1991 |
| EP | 1 004 323 A1 | 5/2000 |
| EP | 1 094 846 A1 | 5/2001 |
| GB | 1 573 995 A | 9/1980 |
| WO | WO-91/06305 A1 | 5/1991 |
| WO | WO-97/16977 A1 | 5/1997 |
| WO | WO-97/35490 A1 | 10/1997 |
| WO | WO-98/03550 A1 | 1/1998 |
| WO | WO-00/03751 A1 | 1/2000 |
| WO | WO-2005/006861 A2 | 1/2005 |

OTHER PUBLICATIONS

Van de Perre, Vaccine 21 (2003) 3374-3376.*
Artym et al., Postepy Hig Med Dosw (online), 2013; 67: 800-816.*
Rahman et al., Human Vaccines & Immunotherapeutics 9:5, 1039-1048; May 2013.*
Lindorfer et al., Immunological Reviews 2001, vol. 183: 10-24.*
Dunman et al., Current Opinion in Pharmacology 2003, 3:486-496.*
Abraham et al., "The influence of periodate oxidation on monoclonal antibody avidity and immunoreactivity," J Immunol Methods. 144(1):77-86 (1991).
Fukumoto et al., "Stability of membrane-sterilized bovine immunoglobins aseptically added to UTH milk," J Food Sci. 59(4):757-59,62 (1994).
Lawton et al., "The synthesis of secretory IgA in the rabbit. I. Evidence for synthesis as an 11 S dimer," J Immunol. 102(3):693-97 (1969).

(Continued)

*Primary Examiner* — Ilia Ouspenski
(74) *Attorney, Agent, or Firm* — Kristina Bieker-Brady; Clark & Elbing LLP

(57) ABSTRACT

The present invention relates to products and methods for preventing, ameliorating and/or treating infections and other diseases. In one aspect, the products of the present invention relates to compositions comprising germ free colostrum. In another aspect, the products of the present invention relates to compositions comprising synthetically multimerized immunoglobulins. In a third aspect, the products of the present invention relates to compositions comprising germ free colostrum enriched with synthetically multimerized immunoglobulins. The invention also relates to use of said compositions as a pharmaceutical e.g. for prophylactic or ameliorating treatment of infections and other diseases. In addition the invention comprises methods for production of said compositions.

5 Claims, 4 Drawing Sheets

(56) References Cited

OTHER PUBLICATIONS

Mainer et al., "Kinetic and thermodynamic parameters for heat denaturation of bovine milk IgG, IgA and IgM," J Food Sci. 62(5):1034-38 (1997).
Mehra et al., "Milk immunoglobins for health promotion," Int Dairy J. 16:1262-71 (2006).
Piot et al., "Preparation of serocolostrum by membrane microfiltration," Le Lait. 84:333-41 (2004).
Su et al., "Extraction of immunoglobulin-G from colostral whey by reverse micelles," J Dairy Sci. 86(5):1639-45 (2003).
Wainwright, "Methylene blue derivatives—suitable photoantimicrobials for blood product disinfection?" Int J Antimicrob Agents. 16:381-94 (2000).
Washburn et al., "Photodynamic inactivation of an RNA enveloped virus in goat colostrum," Small Rum Res. 42:31-7 (2001).
Washburn et al., "The use of phenothiazine dyes to inactivate bovine viral diarrhea virus in goat colostrum," Can J Vet Res. 68(2):105-11 (2004).
International Search Report for International Application No. PCT/DK2009/050016, Aug. 12, 2009 (8 pages).

* cited by examiner

STARTING MATERIAL

A

B

C

METHODS FOR PASSIVE IMMUNIZATION

CROSS-REFERENCE TO RELATED APPLICATIONS

This application is a continuation of U.S. patent application Ser. No. 12/863,745, filed Jul. 20, 2010, with a 371(c) date of Oct. 12, 2010, which is the U.S. national stage filing under 35 U.S.C. §371 of International Application No. PCT/DK2009/050016, filed Jan. 22, 2009, which claims benefit of Danish Patent Application No. PA 2008 00078, filed Jan. 22, 2008, each of which is incorporated by reference.

FIELD OF THE INVENTION

In a first aspect the present invention relates to compositions and methods to improve survival rate and health of newborn mammals particularly farm production animals such as newborn calves, goat's kids, lambs, piglets, foals, chickens, hens, fish and shellfish. Particular compositions according to the invention relates to colostrum and milk, colostrum and milk replacers or supplements treated to inactivate or remove pathogenic infectious agents, such as *Mycobacterium avium* subsp. *paratuberculosis*, while retaining a high content of biologically active immunoglobulins. In a further aspect, which may be combined with the first aspect, the invention relates to colostrum and milk, colostrum and milk replacers or supplements comprising conjugates having antimicrobial activity. The antimicrobial conjugates are obtained by controlled polymerisation and co-polymerisation of substances, such as proteins and peptides, having antimicrobial activity, particularly immunoglobulins.

BACKGROUND OF INVENTION

Colostrum and Passive Immunity

Colostrum is a lactation product produced by the mother after birth (parturition) of mammals such as humans and cows. Typically, the term colostrum milk is used to designate the mammal milk produced for about 5 to 7 days after parturition. Colostrum milk contains an elevated concentration of immunoglobulins compared to normal milk (50-100 gram/L in colostrum compared to 0.5-1.0 gram/L in normal milk). For a range of mammals including cows and pigs the survival of the newborn mammal is critically dependent on the ingestion and successful absorption of immunoglobulins during the first 24 hours after parturition. These mammals are born without circulating antibodies in the blood and need to obtain them by so-called passive immunisation at birth. During the first few hours after parturition the intestine of the newborn is able to absorb the immunoglobulins and transport these to the blood path. An efficient passive immunisation is achieved if the newborn is able to obtain a serum concentration of circulating immunoglobulins in the range of 10-20 gram/L.

Required Colostrum Intake

The amount of colostrum to feed a calf depends on several factors—including the amount of antibody (or immunoglobulin) in the colostrum, the body weight of the calf, the age of the calf at first feeding, and several other factors. In order to calculate the amount (or mass) of IgG that a calf needs, several assumptions may be made, based on existing research data (see list below). The goal is for the calf to obtain a minimum of 10 grams of IgG per liter of serum. A calf's plasma volume at 24 hours of age is approximately 9% of its body weight. To achieve 10 g/L, a newborn calf that weighs 40 kg (about 88 lbs.) must consume 36 grams of IgG from colostrum or a supplement by 24 hours of age. However, IgG is not absorbed with 100% efficiency. Research data suggest the efficiency is closer to 35% (the other 65-70% equilibrates with other body pools or is not absorbed at all). So, to achieve 10 g/L, the calf must consume 103 grams of IgG (36 grams/35%) by 24 hours. If a margin of safety is included in the calculations (achieving a plasma IgG concentration of 15 grams of IgG per liter), the calf needs to consume 154 grams of IgG.

Estimated Colostrum Required by a 40 kq Calf to Achieve Minimum Plasma IgG Concentration.

| | |
|---|---|
| Calf body weight | 40 kg |
| Plasma volume (9% of BW) | 3.6 liters |
| Minimum Plasma concentration | 10 g/L |
| Apparent efficiency of absorption | 35% |
| Required IgG intake | 103 grams |
| Colostral concentration | 50 g/L |
| Required colostrum amount to feed | 2.1 L |

Passive immunity and infectious diseases acquired by the new born from colostrum or milk A key component of the survival and health of calves is colostrum feeding in the first 24 hours of life. Veterinarians and farmers have known for more than one hundred years the importance of colostrum feeding in maintaining the health of young animals, including calves, foals, kids, lambs, pigs, cats and dogs. Research has shown that the absorption of IgG in the first 24 hours of life determines the degree of acquisition of passive immunity and subsequent resistance to disease. The USDA has estimated that nearly 11% of dairy calves in USA die prior to weaning; most of the mortality can be attributed to inadequate colostral IgG intake. The USDA also estimated that 41% of dairy heifer calves have failure of passive transfer at 24 hours of age. The amount of IgG absorbed by the calf is determined by many factors, including the concentration of IgG in colostrum, feeding practices of the farm and metabolic state of the animal. Colostrum is widely variable in IgG concentration, and unfortunately, it is difficult to measure colostral IgG concentration.

The presence of contaminants in colostrum and milk adds a degree of risk to neonatal feeding. Colostrum and milk is recognized as a vector for transmission of a number of disease causing organisms, including the widespread *Mycobacterium avium* subsp. *paratuberculosis* (in short: *Mycobacterium paratuberculosis*) causing Johne's disease in cattle. Farms with significant Johne's infestation often have inadequate supplies of colostrum to feed to their newborn calves. Consequently, farmers are forced to rely on feeding milk replacers and using large amounts of antibiotics to keep the animal alive until its own active immune system can protect it.

*Mycobacterium paratuberculosis* is the agent of a chronic, fatal, granulomatous enterocolitis in ruminants also called *paratuberculosis* or Johne's disease. Johne's disease is a chronic, debilitating intestinal disorder in cattle characterized by diarrhea, reduced feed intake, weight loss and death.

In cattle, the course of the disease is as follows. Calves acquire the infection in the first months of life through oral uptake of colostrum, milk or feces of infected cows. They either successfully clear the infection or become subclinically infected for life. The subclinically infected animals shed the bacteria in their feces intermittently or continuously from an age of approximately two years onward. After an incubation period of four to five years, a proportion of the subclinically infected animals develops an incurable progressive form of protein-losing enteropathy with chronic diarrhea that is ultimately fatal.

A dairy survey conducted by the American National Animal Health Monitoring System suggests that between 20 and 40% of dairy herds in the United States are affected by Johne's disease and it is expected that this figure will continue to increase unless producers implement management regimes that will help control the spread of this disease within their herds. Economic losses are estimated to be $200/infected cow/year and are the result of animal culling, reduced milk production, poor reproductive performance, and reduced carcass value. Johne's disease has become a high priority disease in the cattle industry. The economic impact of this disease on the US dairy industry was estimated to be over $200 million per year in 1996 and is growing each year with the continued spread of this disease. In addition, *M. paratuberculosis* has been implicated as a causative factor in Crohn's disease, a chronic inflammatory bowel disease of human beings, which has served as a further impetus to control this disease in our national cattle.

The neonatal calf is a target for infection with *Mycobacterium paratuberculosis*, the causative agent of Johne's disease. Calves become infected via exposure to the bacterium through contaminated feces, bedding, colostrum, and milk. Shedding of viable *M. paratuberculosis* has been documented in the colostrum and milk of infected dams. However, symptoms of disease do not usually present themselves until the animals reach 3 to 5 years of age or even older. During this time the animal is infected and may be shedding the organism in its feces without showing any clinical signs of disease. In addition to reduced milk production by these animals, they also present a potential infective threat to the rest of the herd. Johne's disease is difficult to manage and control on-farm.

Johne's disease is known to affect cattle, sheep, llamas, camels, goats, farmed deer, bison, and other domestic and wild ruminants. It may be the cause of some wasting diseases in horses and swine. Also, chickens can be successfully infected with it. The disease can also be transmitted to laboratory animals in a laboratory setting. It may also be an agent of the Crohn's disease in humans. There is conflicting information about the zoonotic risks of the disease, but interaction with diseased animals should be done with caution. Johne's is found worldwide.

Johne's disease control programs on dairy farms require testing of cows. Calves born to cows with positive or presumptive positive tests must be removed from the dam to avoid fecal contamination and must be fed colostrum from test negative cows. Unfortunately, many herds are unable to collect sufficient test negative colostrum. In addition, because tests are notoriously unreliable with a test sensitivity that is less than 50%, there is a significant risk that test negative cattle will also shed the Johne's causative organism in colostrum and/or feces.

Most susceptible to infection are animals in their first month of life, although clinical disease becomes apparent only several years later. The main way of infection is the fecaloral route, but since excretion of *M. paratuberculosis* has been demonstrated in colostrum as well as in milk of infected cows, there are strong concerns about feeding such *mycobacteria* loaded colostrum or normal milk to highly susceptible neonate calves.

*Mycobacteria* are notoriously resistant to physical and chemical factors but *M. paratuberculosis* seems to be among the most resistant of *mycobacteria*.

The conventional way of reducing the content of microorganisms in milk is pasteurization and ultra-heat treatment i.e. the milk is exposed to heat for a short period of time. However, the heat treatment does not only destroy the microorganisms present in the milk, but also denatures essential biologically active proteins such as the immunoglobulins.

Several studies have investigated the effect of pasteurisation. The thermal tolerance of *M. paratuberculosis*, specifically the capacity to survive pasteurization, is the subject of considerable interest. Some published reports suggest that *M. paratuberculosis* can survive standard commercial pasteurization while others suggest it cannot. Thermal tolerance curves indicate that *M. paratuberculosis* is comparable in heat resistance to *M. avium* and far more heat resistant than *Listeria*, another facultative intracellular bacterium that is found in raw milk. It has been suggested that *mycobacteria* in milk or colostrum may be killed by pasteurisation at high temperature and thus eliminate the risk of infection of neonates and newborn animals through this route. However, high temperature treatment of immunoglobulin solutions including colostrum has been shown to denature or lead to uncontrolled aggregation and inactivate the biological activity of the immunoglobulins and it seems impossible to perform an efficient and complete elimination of the *mycobacterium* from colostrum or milk under conditions that does not at the same time influence the biological activity of the fragile immunoglobulin molecules present in colostrum. In addition, pasteurizing colostrum at conventional temperatures can result in unacceptable feeding characteristics.

Other important pathogens typically found in colostrum and raw milk include various viruses and bacteria including *Salmonella* spp., *Listeria monocytogenes*, *Escherichia coli*, *Campylobacter* spp., *Streptococcus* spp., *Staphylococcus* spp A method of reducing the bioburden of colostrum by centrifugation has been described in WO97/16977. However, an effective reduction of bacteria requires such a high force of gravitation that proteins might precipitate together with other particles present in a protein rich solution.

Other methods of reducing microbial contaminants in milk are gamma radiation (U.S. Pat. No. 4,784,850) and treatment with β-propiolactone (U.S. Pat. No. 3,911,108). Also, these methods tend to denature proteins to some extent. Sterile filtration is still another method of removing microbes from milk (U.S. Pat. No. 5,256,437; U.S. Pat. No. 5,683,733. Filtration does not usually substantially affect the proteins, but the filters rapidly foul when the solution to be filtered is complex, comprise lipids, colloidal and/or insoluble substances. This is especially a problem with protein rich colostrum, which easily clogs the filters. The problem with clogged filters has previously been solved by partially or completely removing casein from the colostrum, and/or by diluting the colostrum before filtration. Casein can be removed by either acid or enzymatic precipitation, and centrifugation to obtain whey (U.S. Pat. No. 4,644,056 and GB 1,573,995). U.S. Pat. No. 5,670,196 discloses a method of microfiltrering colostrum, whereby defatted colostrum is first acidified to precipitate casein, which is removed by centrifugation, and then the whey is filtered through a charged depth filter to reduce the microorganism content. U.S. Pat. No. 5,707,678 is directed to a similar method, where casein is removed, after which the acidified whey is first ultrafiltered and then microfiltered. The main drawback of these methods is that large amounts of valuable antibodies and other proteins tend to precipitate together with the casein. In addition the removal of casein is a laborious, time consuming and expensive process.

U.S. Pat. No. 5,147,548 discloses a method of sterile-filtering colostrum without previously removing the casein. The optionally defatted colostrum is acidified to a pH of less than 3.5. The casein precipitates at a pH of 5 to 4, but it returns into solution as the pH continues to drop. The acidic solution was found to differ so extensively from the original colostrum that it could be sterile filtered either as such or after neutralizing it back to its original pH. The filter used is a depth filter or a membrane filter. In a preferred embodiment the colostrum is diluted into a sodium chloride solution prior to acidifying. However, also this method has drawbacks. The immunoglobulins are easily inactivated at low pH. Further, the casein precipitation is not fully reversible resulting also in protein loss, and the dilution of the colostrum increases process time and expenses.

WO05006861 deals with disinfecting blood and blood fractions using disinfectant dyes and more specifically with a simple method to destroy a large number of pathogens in human blood prior to transfusion. There is no mentioning of using disinfecting dyes for inactivation of pathogens in colostrum, milk or whey.

EP01094846 is related to the medical field of haematology and, more particularly, for an improved method and device for the removal of disinfectant dyes such as methylene blue from blood, blood fractions or other perishable liquids to which the dyes have been added for disinfecting purposes. The disclosure is silent with regard to the possible application of the method for removal of disinfectant dyes from colostrum, milk or whey.

Thus, there is a need for new methods of inactivating or removing infectious agents, such as *mycobacteria*, in milk and colostrum; milk and colostrum replacers and milk and colostrum supplements without concomitant loss of protective antibody activity and other important qualities.

Accordingly, there is an interest in providing a milk and/or colostrum; milk and/or colostrum replacer and milk and/or colostrum supplement, which has been treated to inactivate or remove infectious agents, such as *mycobacteria*, substantially without loss of protective antibody activity and other important qualities.

Further, there is an interest in providing a method for use of such inactivated products integrated with the general handling of newborn mammals particularly farm production animals such as newborn calves, goats kids, lambs and piglets in order to minimise the risk of infection.

Antimicrobial Compositions (Also Described Herein as Conjugates)

Structurally, antibodies are composed of one or more units, or monomers, each typically portrayed as resembling a Y shape. A monomer contains four polypeptides—two identical copies of a polypeptide known as the heavy (H) chain, and two identical copies of a polypeptide called the light (L) chain. The two heavy chain polypeptides are approximately 440 amino acids long having a molecular weight of about 55,000 daltons each. The two light chains are approximately 220 amino acids long and each having a molecular weight of about 25,000 daltons.

One light chain associates with one heavy chain, and any one antibody molecule will have only one type of light chain and one type of heavy chain. The amino-terminal variable region of a light chain associates with the amino-terminal variable region of one heavy chain to form an antigen binding site. The carboxy-terminal regions of the two heavy chains fold together to make the Fc domain.

The four polypeptide chains of the resulting immunoglobulin molecule are held together by disulfide bridges and non-covalent bonds.

Antibodies are divided into classes—IgG, IgM, IgA, IgE and IgD—on the basis of the type of heavy chain polypeptide they contain. There are only two types of light chain proteins, kappa and lambda. The classes also vary in the number of monomers that join to form a complete antibody molecule.

For example, IgM antibodies have five monomers, each with two antigen binding sites, yielding ten identical antigen binding sites for each molecule.

IgM is thus referred to as decavalent. IgG, IgE, and IgD typically consist of a single monomeric unit and thus are bivalent, and IgA may consist of one, two or more monomers. An antibody's intrinsic affinity is a measure of the strength of its binding to an epitope. In principle, it represents the binding by one antigen binding region, i.e., one-half of a monomer's total binding sites. Avidity, on the other hand, is a measure of the overall stability of the complex between antibody and antigen. Avidity is effected by the intrinsic affinity of the antibody for the epitope, the valency of the antibody and antigen, and the geometric arrangement of the interacting components.

Multivalent interactions may allow low affinity antibodies to bind antigens tightly and can greatly stabilize immune complexes. Thus, antibodies of high avidity may possess increased therapeutic or diagnostic value compared to similar antibodies of low affinity and low avidity In humans, secretion of IgA by the mucosal immune system accounts for 70% of the body's total Immunoglobulin production. The secretory IgA (S-IgA having four antigen binding sites) in the mucociliary blanket is believed to afford protection to mucosal surfaces by neutralizing or otherwise preventing the attachment of viruses, bacteria, and toxins to the mucosal epithelium. In contrast IgG is the predominant immunoglobulin found in the blood.

Mammals, in particular new born calves, suffering from a depressed or an insufficient immune system, or mammals that may be expected to be suffering from a depressed or insufficient immune system may be treated by passive immunisation to control microbial infections. Passive immunisation of humans and animals by intravenous or intramuscular administration of immunoglobulin G is well described in the art for a broad and steadily increasing range of indications.

US application no.: 2005-0191289 discloses non-covalent complexes of immunoglobulins for passive immunisation by systemic absorption through the enteral (oral) and/or transmucosal route. The purpose of the non-covalent complexing with e.g. chitosan is to protect the immunoglobulin against gastrointestinal proteases and acidic environment.

Most disease-causing organisms first enter the body through mucosal surfaces, which is not surprising since the surface area of human mucosae (including the gastrointestinal, genito-urinary, and respiratory tracts) exceeds that of skin by a factor of 200. Most of the antibody that is synthesized daily is secreted by epithelial cells at mucosal surfaces, where it forms a first line of defense against infection. The vast majority of all antibody-secreting plasma cells are located in the intestinal lamina propria, a layer of cells underlying the epithelial cell layer. These plasma cells produce more IgA than all other immunoglobulin isotypes combined (in humans, 40-60 mg/kg/day). The IgA is secreted as polymeric IgA (SIgA), which is comprised mostly of IgA dimers (4 heavy chains and 4 light chains), linked together by a protein called the joining, or J chain.

Complexes of SIgA and antigen are removed from the body by physical mechanisms, such as peristalsis and mucociliary transport in the gastrointestinal and respiratory tracts.

In contrast to vaccines, passive immunization can deliver protective levels of antibodies directly to the susceptible mucosal site where most infections begin. Passive protection by transfer of antibody from maternal origin represents in many species including humans an efficacious and specific mechanism to prevent mucosal infection in newborns lacking a fully matured immune system. This takes place by ingestion of breast milk containing SIgA antibodies induced by natural exposure of the maternal immune system to environmental microbes.

The natural protection offered by passive immunization has already provided the physicians with the opportunity to envisage treatments against mucosal infectious agents with antibody-enriched milk, serum or egg yolk preparations (examples in Table 1).

Even though SIgA is secreted at high rates at the mucosal surfaces there is no easy route to isolate and produce concentrates of SigA for use in large scale passive immunisation programs.

SIgA has been produced in transgenic plants and by other genetically modified organisms. However, these attempts to source this type of antibody are still very expensive to realise commercially and for each new antibody specificity there is a need for a corresponding transgenic or other genetically

TABEL 1

Examples of Immunotherapy by Administration of Antibody Onto Mucosal Surfaces

| Type of Ig Delivered | Infection | Infectious Agent | Targeted Antigen | Target Organism |
|---|---|---|---|---|
| IgG | Respiratory tract infection | Respiratory syncytial virus | F glycoprotein, GP 84 | Mouse |
| IgG2a | Dental caries | Streptococcus mutans | SA I/II | Human |
| IgA | Respiratory tract infection | Sendai virus | HN protein | Mouse |
| SIgA | Streptococcal infection | Group A Streptococci | M protein | Mouse |
| IgA, IgG | Necrotizing enterocolitis | — | Multiple | Human |
| IgG, IgM, IgA | Meningoccocal infection | *E. coli* K1 | b-polysaccharide | Rabbit |
| IgA | Flu | PR8 Influenza virus | Hemagglutinin | Mouse |
| IgA, IgG | Respiratory tract infection | Sendai virus | Multiple | Mouse |
| IgA | Pseudomembranous colitis | *Clostridium difficile* | Multiple | Human |
| IgA | Gastritis, duodenal ulcers | *Helicobacter felis* | Multiple | Mouse |
| IgA | Diarrhea | *Campylobacter jejuni* | Multiple | Human |
| IgA, SIgA | Cholera | *Vibrio cholerae* | Lipopolysaccharide | Mouse |
| Fab (LI) | Respiratory tract infection | Respiratory syncytial virus | F glycoprotein | Mouse |
| IgA | Cholera | *Vibrio cholerae* | Lipopolysaccharide | Mouse |
| IgY | Diarrhea, gastroenteritis | Rotavirus | Multiple | Calf |
| IgA | Respiratory tract infection | Respiratory syncytial virus | F glycoprotein | Mouse |
| IgA | Gastritis, duodenal ulcers | *Helicobacter felis* | Urease | Mouse |
| IgA | Dysentery | *Shigella flexneri* | Lipopolysaccharide | Mouse |
| IgA | Respiratory tract infection | Respiratory syncytial virus | F glycoprotein | Monkey |
| IgG | Respiratory tract infection | Respiratory syncytial virus | F glycoprotein | Calf |
| IgA | Sexually transmitted disease | *Chlamydia trachomatis* | Major OMP | Mouse |
| IgG, IgA | Rhinitis | — | Multiple | Human |
| IgG, SIgA/G | Dental caries | *Streptococcus mutans* | SA I/II | Human |
| IgY | Pseudomembranous colitis | *Clostridium difficile* | Toxin A, Toxin B | Hamster |
| IgA | Diarrhea | *Cryptosporidium parvum* | P23 | Mouse |
| IgG, IgA | Respiratory tract infection | Respiratory syncytial virus | F glycoprotein | Mouse |
| IgG1 | Respiratory tract infection | Respiratory syncytial virus | F glycoprotein | Rat |
| SIgA | Dysentery | *Shigella Flexner* | Lipopolysaccharide | Mouse |

SIgA has a number of advantages over the monomeric IgG for passive immunization at skin and mucosal surfaces. First, the presence of four antigen binding sites confers an increase in avidity. Second, SIgA is more resistant than IgG or monomeric IgA to the proteolytic enzymes found in the gastrointestinal tract.

For passive immunization at skin and mucosal surfaces to afford protection against infection, it is likely that a few milligrams/kg will be required daily during some susceptible period, whereas systemic clearance of an existing infection might require much higher amounts.

modified organism. In addition, even though the antibody produced may be identical to the antibodies corresponding to the species of application, there is a strong demand to remove any contaminating host antigens that may evoke allergic or other adverse reactions.

WO9106305 discloses the preparation of oligomeric monoclonal immunoglobulin G with high avidity for antigens. The oligomeric antibodies are produced by the use of genetically engineered organisms and are typically no more than tetra or hexalent with respect to antigen binding sites. Again, this approach to prepare high avidity antibodies is very expensive to realise commercially and still for each new antibody specificity there is a need for a corresponding genetically modified organism. In addition, even though the antibody produced may be identical to the antibodies corresponding to the target species of final therapeutic application, there is a strong demand to remove any contaminating host antigens that may evoke allergic or other adverse reactions.

IgG and monomeric IgA, however is available for isolation on a large scale and at low cost from e.g. human and animal blood plasma and milk. Particularly large amounts of IgG are available in the bovine milk industry. One liter of milk or whey from the cheese industry may provide 300-1000 mg IgG and is therefore available in sufficient quantities to support an industrial production of products for passive immunisation. Likewise animal plasma from slaughterhouses is abundant and contains a high concentration of IgG and IgA. Human plasma is systematically collected from blood transfusion centers and is available commercially for the isolation of immunoglobulins as well. The antibodies present in all of these raw materials has polyvalent antigen binding specificity reflecting the environment and exposure to diverse antigens of the host and pooling of blood or milk from several hosts will create a very broad antibody specificity thus eliminating the need for individual production of monoclonal antibody preparations. In certain instances it may even be advantageous to vaccinate the hosts (animals or humans) in order to provoke an immune response against a particular antigen or microorganism—or a cocktail of antigens or microorganisms.

Another group of substances exhibiting antimicrobial activity is a non-immunoglobulin substance, such as Lactoferrin.

Mammary fluids, colostrum and milk, deliver nature's first host defense systems upon birth, and these essential liquids are critical for survival of the neonate. The identification and characterization of substances, such as anti-infectious proteins, were among the early scientific discoveries and this group of proteins has long been recognized for promoting health benefits in both newborns and adults. Among the more widely studied are the immunoglobulins, lactoperoxidase, lysozyme, and lactoferrin.

"Antimicrobial peptide" ("AmP"), as used herein, refers to oligopeptides, polypeptides, or peptidomimetics that kill (i.e., bacteriocidal) or inhibit the growth of (i.e., bacteriostatic) microorganisms including bacteria, yeast, fungi, mycoplasma, viruses or virus infected cells, and/or protozoa. In some instances, AmPs have been reported to have anticancer activity. Generally antimicrobial peptides are cationic molecules with spatially separated hydrophobic and charged regions. Exemplary antimicrobial peptides include linear peptides that form an α-helical structure in membranes or peptides that form β-sheet structures optionally stabilized with disulfide bridges in membranes. Representative antimicrobial peptides include, but are not limited to, cathelicidins, defensisn, dermeidin, and more specifically magainin 2, protegrin, protegrin-1, melittin, 11-37, dermaseptin 01, cecropin, caerin, ovispirin, and alamethicin. Naturally occurring antimicrobial peptides include peptides from vertebrates and non-vertebrates, including plants, humans, fungi, microbes, and insects.

Lactoferrin is one of the principal proteins responsible for providing protection to infant mammals before their immune systems begin to function. It is a minor protein in cow's milk (100-300 mg/L) and is extracted from skim milk or whey through protein separation. As an iron-binding glycoprotein of the transferrin family, Lactoferrin is found in high concentrations in mother's milk. It is used throughout the US, Europe and Asia as a nutritional supplement or as an additive to infant formula.

Apart from milk, lactoferrin is generally produced and released in the body in the digestive, respiratory and reproductive systems through saliva, tears, nasal secretions, etc. Lactoferrin is also produced by a special group of white blood cells known as neutrophils.

The presence of lactoferrin in these biological fluids points to lactoferrin's primary role as the principal gatekeeper of the non-specific defense system against invading pathogens and other disease causing agents.

Most of the biological activity of lactoferrin is believed to be related to its excellent iron binding properties, but many non-iron binding related effects have been described as well.

With respect to its role as a primary pathogen defense protein, research supports the following important functionalities:

Antimicrobial activity, including Gram positive and Gram negative bacteria, yeast and fungi Anti-viral activity, including cytomegalovirus, influenza, HIV and rotavirus Anti-oxidant activity, protects the white blood cells against free iron catalyzed oxidation reactions Immune system enhancement, controls the body's immune response during infection and inflammation.

The antimicrobial activity of lactoferrin has several working mechanisms:

Lactoferrin binds iron which is an essential element for bacterial growth. Bacterial cells become iron deprived and stop growing.

Lactoferrin binds to bacteria and, as a consequence, the microbial cell membrane loses its integrity and the bacteria is killed.

Lactoferrin stimulates phagocytosis or microbial destruction by macrophages and monocytes.

Lactoferrin eliminates and prevents bacteria from forming essential attachment structures making them incapable of colonizing and multiplying.

Many scientific studies have demonstrated these potent antimicrobial effects. Recent studies also show an important potentiating effect of lactoferrin with antibiotics and antifungal agents. In vivo results from animal studies are available as well. Bovine lactoferrin was shown to have a bacteriostatic effect in mice infected with either Enteric pathogens or Clostridia. In humans the duration and severity of enteric infections decreased when patients were treated orally with lactoferrin. Bacterial infections in rainbow trout could be reduced by oral administration of bovine Lactoferrin.

Recently a significant amount of attention has been given to the antiviral activity of lactoferrin. The mechanism of action appears to be the inhibition of the absorption process of the virus particle to the mammalian host cell, either through binding to the host cell or to the virus itself. Published scientific studies have clearly demonstrated the protective effects of lactoferrin against HIV and cytomegalovirus, Herpes simplex type 1 and 2, hepatitis C, influenza and rotavirus. Interestingly, the first in vivo animal studies support the findings from the in vitro work. When mice were pretreated with bovine lactoferrin and challenged with mouse cytomegalovirus it did not result in the typical 100% mortality. The mechanism behind this protective effect is related to the stimulation of natural killer cell activity (phagocytosis).

Neutrophils, monocytes and macrophages are cells of the immune system that kill invading pathogens by oxidation reactions. Free iron is often present in areas of inflammation or infection. Oxidation reactions are accelerated by the catalytic effect of iron on free radical production. Lactoferrin binds the free iron with extremely high affinity and thus functions as a powerful local antioxidant protecting the immune cells against the free radicals produced during the inflammatory response. Although only the neutrophils produce and deliver lactoferrin, monocytes and macrophages have lactoferrin receptors on their cell surfaces.

One of the most potent stimulants of cytokine activity, (compounds produced by immune cells during infection and inflammation to coordinate the defense against pathogens), is the endotoxin LPS. This microbial membrane derived lipopolysaccharide (LPS) is bound and neutralized by lactoferrin and down regulates the immune response before it can get out of control as is the case with autoimmune disease. Both in vitro and in vivo studies have shown these protective and stimulatory effects of Lactoferrin.

Lactoferrin in a polymerised (complexed) form has been introduced commercially for the treatment of meat surfaces (e.g. carcasses) in the food industry. The product called Activin from aLF Ventures is apparently based on a non-covalent interaction between Lactoferrin and naturally occurring polysaccharides. The Activin product is claimed to be one thousand times more effective in inhibiting attachment of pathogenic bacteria than normal monomeric Lactoferrin.

U.S. Pat. No. 6,172,040 disclose a method for treating products, such as meat products, with immobilized lactoferrin to reduce microbial contamination. The lactoferrin is immobilized on a naturally occurring substrate, preferably a galactose-rich polysaccharide, via the N-terminal region. In some embodiments, the lactoferrin is applied as an aqueous solution containing a mixture of the immobilized lactoferrin and native lactoferrin, and a buffer system that includes a physiologically acceptable acid, such as citric acid, a physiologically acceptable base, such as sodium bicarbonate, and a physiologically acceptable salt, such as sodium chloride. There is no mentioning or teaching of a covalent bonding of Lactoferrin to the substrate and all examples given in the disclosure are based on non-covalent—and therefore reversible—interactions.

However, the stability of the complex between Lactoferrin and a substrate such as a polysaccharide can be highly critical for the efficiency of the Lactoferrin. Any reversibility in the complex towards the monomeric Lactoferrin will lead to a diminished effect. This will be particularly relevant in cases where a Lactoferrin complex may be exposed to extreme pH values and/or an ionic strength high enough to dissociate the non-covalent interactions keeping the complex intact (such as passage through the stomach and the gastrointestinal tract or exposure to other mucosal surfaces).

Accordingly, what is needed in the art is a Lactoferrin complex having a covalent structure and a fixed high molecular weight providing enhanced anti-microbial activity of Lactoferrin under challenging pH and salt conditions.

Thus, it is of interest to provide a germ free composition comprising colostrum, a composition comprising synthetically multimerised immunoglobulins, having antimicrobial activity and high avidity and yet which avoid many of the difficulties and costs associated with the isolation of similar substances on a large scale or preparation of genetically engineered organisms giving narrow antigen binding specificities. Furthermore, it is of interest to provide a more clinically effective and commercially viable product for passive immunisation of skin, skin lesions, surgical wounds and mucosal surfaces.

SUMMARY OF INVENTION

The present invention relates to compositions and methods to improve the health of subjects, for example animals and humans. In particular farm production animals such as newborn calves, piglets, goat's kids, lambs but also hens and chickens and fish can benefit from the compositions and methods of the present invention. The compositions relate to germ free colostrum, supplements to increase resistance to pathogenic infections, comprising synthetically multimerised immunoglobulins, however, also a composition comprising colostrum, enriched with synthetically multimerised immunoglobulins is provided.

In a first aspect, a method is provided for producing a germ free composition, comprising the steps of i) providing colostrum, part or derivative thereof, ii) mixing the colostrum of step i) with at least one disinfectant dye, iii) obtaining a composition that is free of pathogenic microorganisms.

The colostrum may be of any origin, however, particular embodiments pertains to colostrum of bovine, porcine, ovine and/or human origin.

In a second aspect the present invention discloses a germ free composition obtainable by, or obtained by, a method for producing germ free composition, comprising the steps of i) providing colostrum, part or derivative thereof, ii) mixing the colostrum of step i) with at least one disinfectant dye, iii) obtaining a composition that is free of pathogenic microorganisms.

A third aspect pertains to a germ free composition, comprising colostrum, part or derivatives thereof, comprising at least 80% active native immunoglobulins.

A fourth aspect relates to a germ free composition, comprising colostrum, parts or derivatives thereof and at least one disinfectant dye.

A fifth aspect pertains to a composition comprising immunoglobulins, part or fragments thereof, wherein said immunoglobulins are synthetically multimerised. In a particular embodiment the synthetically multimerised immunoglobulin is immunoglobulin G. The synthetically multimerised immunoglobulins comprise at least one cross-linking covalent chemical bond between individual immunoglobulins.

Another aspect relates to a method for producing synthetically multimerised immunoglobulin comprising the steps of
  i) providing a starting material
  ii) isolating immunoglobulin, part or fragments thereof
  iii) multimerising the isolated immunoglobulin of step ii)
  iv) obtaining multimerised immunoglobulin or
  v) providing a starting material
  vi) multimerising components of the starting material of step v)
  vii) optionally, isolating immunoglobulin, part or fragments thereof
  viii) obtaining multimerised immunoglobulin.

The starting material is milk, colostrum, whey, serum, plasma, eggs or any part or derivates thereof.

The multimerisation step involves cross-linking of the starting material and/or immunoglobulins catalysed by cross-linking agents such as for example periodate or periodate forming compounds.

Yet another aspect relates to a composition obtainable by, or obtained by the method for producing synthetically multimerised immunoglobulin.

Within the scope of the present invention is a germ free colostrum composition enriched with the composition comprising synthetically multimerised immunoglobulin. Thus in one aspect the present invention concerns a composition comprising i) a composition comprising germ free colostrum, part or fragment thereof and ii) composition comprising synthetically multimerised immunoglobulin as described in the present invention.

The compositions of the present invention are useful in a number of applications relating to resistance to pathogenic infections, in particular to *Mycobacterium paratuberculosis*; for passive immunisation, wound healing, and skin diseases.

Thus, aspects relate to a pharmaceutical composition comprising the compositions as disclosed herein and optionally a pharmaceutically acceptable carrier, a food supplement comprising the composition as defined herein, a dietary composition comprising the compositions as disclosed herein, an infant formulation comprising the compositions as disclosed herein, a growth promoter comprising the composition as disclosed herein, a milk replacer comprising the compositions as disclosed herein.

Aspects relate to a method for preventing, ameliorating and/or treating pathogenic infections comprising administration of the compositions as disclosed herein in a therapeutically effective amount to a subject in need thereof, a pharmaceutical composition for preventing, ameliorating and/or treating pathogenic infections comprising the compositions as disclosed herein, a method for passive immunisation of a subject comprising the step of administering the composition as disclosed herein in an effective amount to a subject.

Further aspects relate to use of the compositions as disclosed herein for the manufacture of a medicament for the prevention, amelioration and/or treatment of pathogenic infection, compositions as disclosed herein for the prevention, amelioration and/or treatment of pathogenic infection, use of the compositions as disclosed herein for the manufacture of a medicament for passive immunisation of a subject, composition as disclosed herein for passive immunisation. Aspects of the present invention also relate to pharmaceutical compositions for passive immunisation comprising the compositions as disclosed herein.

Additional aspects of the present invention relates to a method for the prevention, amelioration and/or treatment of infection in subjects suffering from diseases suppressing the immune system, said method comprises the step of administering a pharmaceutical effective amount of the composition comprising synthetically multimerised immunoglobulins of the present invention, use of the composition comprising synthetically multimerised immunoglobulins for the manufacture of a medicament for the prevention, amelioration and/or treatment of infection in subjects suffering from diseases suppressing the immune system, a composition comprising synthetically multimerised immunoglobulins for the prevention, amelioration and/or treatment of infection in subjects suffering from diseases suppressing the immune system, use of the composition comprising synthetically multimerised immunoglobulins for the manufacture of a medicament for infection in subjects suffering from diseases suppressing the immune system, composition comprising synthetically multimerised immunoglobulins in subjects suffering from diseases suppressing the immune system.

Yet further aspects related to a pharmaceutical composition for preventing, ameliorating and/or for infection in subjects suffering from diseases suppressing the immune system, comprising the composition comprising synthetically multimerised immunoglobulins, a method for preventing, ameliorating and/or treating wounds, said method comprising the step of administering a pharmaceutically effective amount of the composition comprising synthetically multimerised immunoglobulins to a subject in need thereof, a method for preventing, ameliorating and/or treating skin diseases, said method comprising the step of administering a pharmaceutically effective amount of the composition comprising synthetically multimerised immunoglobulins to a subject in need thereof. Another aspects pertain to use of the compositions of the present invention as a growth promoter for a subject, use of the compositions of the present invention as a milk replacer for a subject, use of the compositions of the present invention as a food supplement for a subject, use of the compositions of the present invention as a dietary composition for a subject, use of the compositions of the present invention as an infant formulation for a subject.

DETAILED DESCRIPTION OF THE INVENTION

Figure 1:
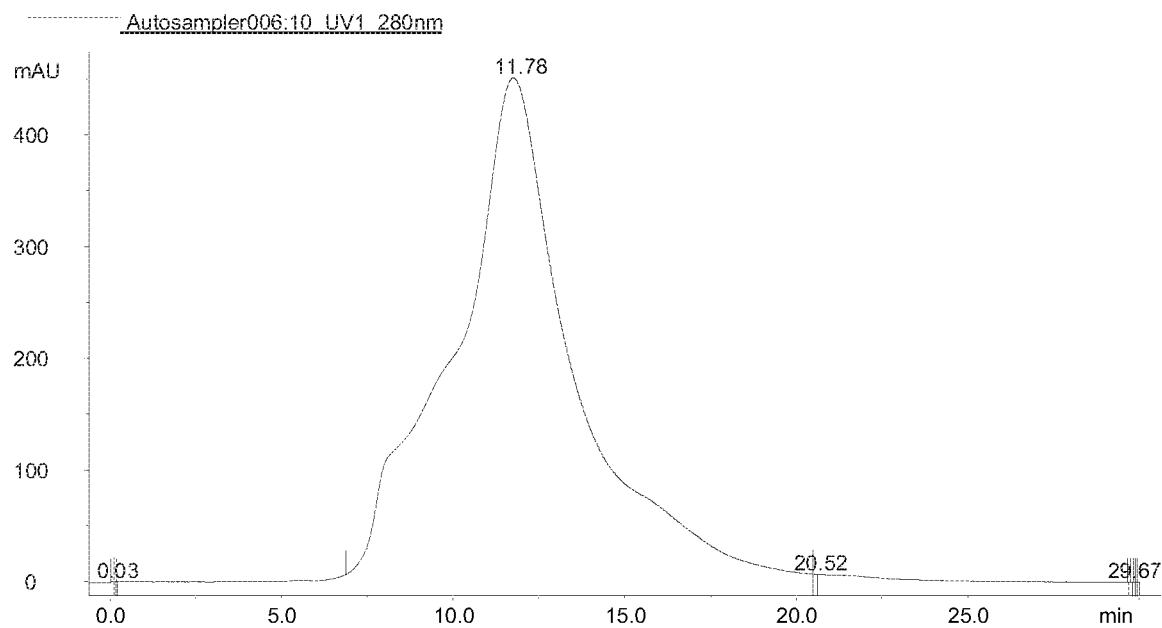
FIG. 1 illustrates the UV trace (280 nm) of gel permeation chromatography analysis of the Concentrated IgG Eluate according to example 1.

The present invention relates to methods for production and compositions that may be used to increase the resistance to pathogenic infection, in subjects such as animals but also in humans.

One aspect relates to a method for producing a germ free composition, comprising the steps of i) providing colostrum, part or derivative thereof, ii) mixing the colostrum of step i) with at least one disinfectant dye, iii) obtaining a composition that is free of pathogenic microorganisms. The colostrum, part or derivative thereof of step i) is of bovine, porcine, ovine and/or human origin.

Colostrum is a form of milk produced by mammals in late pregnancy and the few days after giving birth. Colostrum is high in carbohydrates, in particular lactose, protein, and antibodies (immunoglobins). Colostrum contains all five immunoglobulins found in all mammals, (A, D, G, E and M) and the total amount of immunoglobins may be up to 10% or even up to 30% of the total protein content in colostrum. Other proteins in colostrum include casein, lactoferrin, lactalbumin, lactoglobin, lactoperoxidase and growth factors, in particular IGFs, and peptides such as PRPs (proline rich polypeptides). In addition, colostrum contains fat, vitamins, and nutrients.

In one embodiment of the present invention, the colostrum, part thereof or derivative thereof, originates from bovine, equine, porcine, human, ovine, caprine or cervidae. However, in another embodiment the colostrum or part thereof is of bovine, porcine, ovine or human origin. In a preferred embodiment the colostrum is of bovine origin.

According to the present invention, the composition comprises whole colostrum or part thereof. The main components of colostrum are fat, protein, lactose, minerals, immunoglobulins (IgA, IgD, IgG, IgE and IgM), lactoferrin, water and fat soluble vitamins, respectively. An example of the distribution of the main components of bovine colostrum is given below:

Example of the Distribution of the Main Components of Bovine Colostrum

| | |
|---|---|
| Fat | 6.7% w/w |
| Protein | 14.9% w/w |
| Lactose | 2.5% w/w |
| Ash (minerals) | 0.05% w/w |
| Immunoglobins | 47.5 mg/ml |
| Lactoferrin | 0.8 mg/ml |
| Vitamins (fat soluble) | 8.0 µg/ml |
| Vitamins (water soluble) | 6.8 µg/ml |

The composition of the present invention comprises for example parts of whole colostrum. In one embodiment fats and/or cassein and/or lactose is removed from the colostrum. In another embodiment the composition comprises immunoglobulins and lactoferrin of colostrum. For example the composition comprises at least IgA, IgM and lactoferrin of colostrum. In another embodiment the composition of the present invention comprises at least least IgA, IgM, IgG and lactoferrin of colostrum. In yet another embodiment the composition of the present invention comprises at least IgA, IgM, IgG, lactoferrin and beta-lactoglobulin of colostrum. In a further embodiment the composition of the present invention comprises at least IgA, IgM, IgG, lactoferrin, beta-lactoglobulin and alpha-lactalbumin of colostrum.

In preferred embodiments colostrum, part or derivative thereof of step i) is colostrum obtained from bovine, porcine, or human subject within 48 hours after giving birth.

In a preferred embodiment the compositions of the present invention comprises at least IgA, IgM, IgG, lactoferrin, beta-lactoglobulin, alpha-lactalbumin and IGF-1 of colostrum.

In one embodiment the composition of the present invention comprises the following components in the following amounts of total proteins of colostrum: Lactoferrin in a concentration between 0.1-1.0 mg/ml, beta-lactoglobulin in a concentration between 1-4 mg/ml, alpha-lactalbumin in a concentration between 0.1-2 mg/ml, IgG in a concentration between 1-10 mg/ml, IgA in a concentration between 0.05-3.00 mg/ml, IgM in a concentration between 0.05-4.00 mg/ml and IGF-1 in a concentration between 1-15 ng/ml.

In another embodiment the composition of the present invention comprises the following components in the following amounts of total proteins of colostrum: Lactoferrin in a concentration between 10-50 µg/ml, beta-lactoglobulin in a concentration between 2000-3000 ng/ml, alpha-lactalbumin in a concentration between 2000-3000 ng/ml, IgG in a concentration between 3-8 mg/ml, IgA in a concentration between 0.08-2.00 mg/ml, IgM in a concentration between 1-3 mg/ml and IGF-1 in a concentration between 2-10 ng/ml.

In a preferred embodiment the composition of the present invention comprises the following components in the following amounts of total bioconjugated proteins of colostrum: Lactoferrin in a concentration of at least 35 µg/ml, beta-lactoglobulin in a concentration of at least 2300 ng/ml, alpha-lactalbumin in a concentration of at least 2200 ng/ml, IgG in a concentration of at least 4 mg/ml, IgA in a concentration of at least 0.15 mg/ml, IgM in a concentration of at least 1 mg/ml and IGF-1 in a concentration of at least 5 ng/ml.

In another embodiment the present invention relates to compositions, wherein the concentration of immunoglobulin corresponding to a at least 10%, such as at least 15%, such as at least 20%, such as at least 25%, such as at least 30%, such as at least 35%, such as at least 40%, such as at least 45%, such as at least 50%, for example 55%, on a dry matter basis.

Colostrum may be collected from the birth-giving animal a few days before to some days after delivery of the offspring. In one embodiment of the present invention the colostrum used for the preparation of the composition is colostrum or part thereof collected up to 72 hours after delivery of the offspring. However, in a preferred embodiment of the present invention, the colostrum or part thereof is collected up to 48 hours of delivery.

The method comprises a step of mixing the colostrum of step i) with at least one disinfectant dye. In one embodiment the disinfectant dye is an artificial organic dye. The at least one disinfectant dyeis selected from the group consisting of methylene blue and related thionine dyes, acridine orange, acridine yellow and related acriflavine (acridine) dyes, proflavine hemisulphate, quinacrine and its derivatives, brilliant green, gentian violet, crystal violet and related triphenyl methane dyes, bis naphthalene dyes such as trypan blue and trypan red, and/or combinations thereof. It is appreciated that any of the listed artificial organic dyes may be used in separate embodiment and/or combinations. It is further anticipated that at least one, such as at least two, such as at least three disinfectant dyes, for example at least four disinfectant dyes, such as at least five disinfectant dyes, such as at least six disinfectant dyes, for example at least seven disinfectant dyes, such as at least eight disinfectant dyes, such as at least nine disinfectant dyes, for example at least ten disinfectant dyes.

In a preferred embodiment of the present invention, the chemical substance(s) may comprise solutions of "Double dye" (methylene blue plus crystal violet) by adding a stock solution containing equal weight percentages of the two dyes. For example, a double dye stock solution of 1% by weigh of each of the dye may be conveniently used. In a particular embodiment the disinfectant dyes are a combination of methylene blue and crystal violet.

The cause of the disinfectant property of these dyes is not entirely known. Since many of the disinfectant dyes have oxidation-reduction (redox) potentials in the range of many electron transport components of oxidative metabolism, it seems possible that these dyes may operate by "short circuiting" electron transport pathways. Generally, the dyes show differential activity towards Gram-negative versus Gram-positive bacteria with electronegative (acidic) dyes being more effective on Gram-negative bacteria and electropositive (basic) dyes being more effective on Gram-positive bacteria such as *Staphylococcus aureus*.

Although the dyes are considered safe in regard to intake by humans and annimals, in one embodiment of the invention the at least one disinfectant dye is removed before administering the compositions of the present invention according to the present method.

This can be accomplished by a variety of filters and binding materials. According to the present invention removal with polyvinyl acetal (PVA) and/or with polyvinyl alcohol-acetal (PVAA) is a preferred method, although the other removal methods well known in the art such as ion exchange are also useable. Thus, in one embodiment of the present invention the method comprises the method of a further step of removing the at least one disinfectant agent of step ii). The at least one disinfectant agent may be removed by the use of a polymer such as polyvinyl alcohol-acetal.

After dye exposure of the product of the present invention according to the "Double dye"-method described above, the product of the present invention is then filtered through a polyvinyl acetal (PVA) and/or polyvinyl alcohol-acetal (PVAA) filter column in order to remove the dyes—both of which bind strongly to the PVA and PVAA material.

In one embodiment the method according to the present invention comprises a further step of adding at least one further chemical substance selected from reducing agents (antioxidant) and/or cell lysing agents. An antioxidant is a molecule capable of slowing or preventing the oxidation of other molecules. Oxidation is a chemical reaction that transfers electrons from a substance to an oxidizing agent. Oxidation reactions can produce free radicals, which start chain reactions that damage cells. Antioxidants terminate these chain reactions by removing free radical intermediates, and inhibit other oxidation reactions by being oxidized themselves. As a result, antioxidants are often reducing agents.

The compositions of the present invention may further comprise an antioxidant (reducing agent), such as ascorbic acid, sulfites, oxalic acid and oxalates in combination with one or more disinfectant dyes. In a preferred embodiment of the present invention, the reducing agent is ascorbic acid.

In a preferred embodiment the at least one reducing agent is ascorbic acid. The best results are obtained by adding sufficient reducing agent in the form of ascorbic acid (vitamin C) or its close derivatives to result in the diluted dye solution being decolorized. Generally, a weight percentage of added ascorbate equal to the combined weights of the added dye is sufficient. In some cases, the sample may be especially poor in natural reducing agents (as indicated by an obvious blue color after dye and ascorbate addition) so that additional ascorbate must be added to reduce the color.

In addition, the compositions of the present invention may further comprise a cell lysing agent capable of destroying the cell membrane and/or cell wall of cells, for example bacteria cells. Such cell lysing agent may be a detergent, for example sodium dodecyl sulphate, sodium lauroyl sarcosinate and deoxycholate.

In a preferred embodiment the at least one detergent agent is sodium dodecyl sulphate.

In an embodiment the treatment with one or more chemical substances is performed at an elevated temperature in order to efficiently kill pathogenic microorganisms. However the temperature should be kept below the denaturing point for the immunoglobulins. Thus, the preferred temperature range for the treatment is within 15-65° C., such as 25-60° C., such as 35-60° C., such as 40-57° C., such as 45-56° C., such as 50-56° C. In still a preferred embodiment the treatment is performed at a temperature of at least 15° C., such as at least 25° C., such as at least 35° C., such as at least 40° C., such as at least 45° C., such as at least 50° C., such as at least 55° C.

In one embodiment the at least one further chemical substance is removed in yet another step. In still a preferred embodiment one or more or all of the chemical substance(s) have been removed from the product after inactivating the pathogenic microorganism(s). A preferred way of removing the chemical substance(s) is by way of adsorption to a solid phase.

In one embodiment, the colostrum, part or derivative thereof in a further step is multimerised by at least one cross-linking agent.

Synthetic Cross-Linking and Polymerisation/Multimerisation

Cross-linking agents catalyse the formation of cross-linking that is the covalent chemical bond that link one polymer/multimer chain to another.

According to the present invention, the process of synthetically cross-linking is referred to as "synthetic polymerisation" and/or "synthetic multimerisation".

Polymer/multimer chains can refer to synthetic polymers/multimers, or to natural polymers/multimers (such as proteins, polysaccharides etc.). The cross-linking agent (or cross-linker) refers to the compound that mediates the chemical bonding of two or more polymer/multimer chains. Alternatively, bonds are formed within one polymer/multimer chain. It is appreciated that the cross linking thus occurs between two or more polymer/multimer chains, and/or within one polymer/multimer chain.

It is beneficial to multimerise the entire proteins from colostrum rather than just a few proteins, as the combination of the proteins is necessary for the healing processes in relation to the properties of the compositions of the present invention towards prevention, ameliorating and/or treating pathogenic infections.

According to one aspect of the present invention, the cross-linking comprises the formation of polymerised/multimerised colostrum, parts of colostrum or derivatives of colostrum.

In one embodiment of the present invention the cross-linker is selected from EGS (Ethylene glycol bis[succinimidylsuccinate]), Sulfo EGS (Ethylene glycol bis[sulfosuccinimidylsuccinate]), C6-SANH (C6-succinimidyl 4-hydrazinonicotinate acetone hydrazone), SANH (succinimidyl 4-hydrazinonicotinate acetone hydrazone), C6-SFB (C6-succinimidyl 4-formylbenzoate), BSOCOES (Bis[2-(succinimidyloxycarbonyloxy)ethyl]sulfone), DSP (Dithiobis[succinimidyl propionate]), DTSSP (3,3"-Dithiobis[sulfosuccinimidylpropionat]), DTBPD (Dimethyl 3,3"-dithiobispropionimidate•2 HCl), DSS (Disuccinimidyl suberate), BS (Bis[sulfosuccinimidyl]suberate), DMS (Dimethyl Suberimidate•2 HCl), DMP (Dimethyl pimelimidate•2 HCl), DMA (Dimethyl adipimidate•2 HCl), SHTH (Succinimidyl 4-hydrazidoterephthalate hydrochloride), DSG (Disuccinimidyl glutarate), MSA (Methyl N-succinimidyl adipate), DST (Disuccinimidyl tartarate), SFB (Succinimidyl 4-formylbenzoate), DFDNB (1,5-Difluoro-2,4-dinitrobenzene), DSP (Dithiobis[succinimidyl propionate]), DTSSP (3,3"-Dithiobis[sulfosuccinimidylpropionate]), EDC/NHS, glutaraldehyde, dihydroxyacetone, phenyl azide, tyrosinase, transglutaminase and/or periodate.

In another embodiment of the present invention, the cross-linking agent is selected from EDC/NHS or derivatives thereof, glutaraldehyde or derivatives thereof, transglutaminase or derivatives thereof, tyrosinase or derivatives thereof, and/or dihydroxyacetone or derivatives thereof.

In yet other embodiments the cross-linking agent is dihydroxyacetone or derivatives thereof, the cross-linking agent is EDC/NHS or derivatives thereof, the cross-linking agent is glutaraldehyde or derivatives thereof, the cross-linking agent is transglutaminase or derivatives thereof, the cross-linking agent is glutaraldehyde or derivatives thereof, the cross-linking agent is transglutaminase or derivatives thereof, the cross-linking agent is tyrosinase or derivatives thereof.

In a particular embodiment the cross-linking agent is periodate or a periodate forming agent, such as sodium periodate, potassium periodate, lithium periodate and calcium periodate. In a preferred embodiment the cross-linking agent is sodium periodate.

Polymerisation/Multimerisation of Biomolecules with Periodate or Periodate Forming Agents Biomolecules that possess carbon—carbon bonds bearing an amine moiety adjacent to a hydroxyl moiety or diols, such as cis-diols, are oxidizable with periodate. A carbon—carbon bond bearing an amine moiety adjacent to a hydroxyl moiety is known as a 2-aminoalcohol moiety. The 2-aminoalcohol or cis-diol moiety is oxidizable with periodate, which can be provided as periodic acid or salts thereof, such as sodium periodate, potassium periodate, or other alkali metal periodates. Typically, a stoichiometric amount of periodate is used to oxidize the 2-aminoalcohol moiety, although an excess could be used. Periodate may also be produced in situ by electrochemical oxidation of iodate. In this way the periodate concentration may be maintained by continuous electrochemical regeneration. Oxidation of such biomolecules forms reactive aldehyde moieties within the biomolecules.

The oxidation is carried out in an aqueous solution, preferably an aqueous buffered solution, at a temperature that does not destroy the biological properties of the biomolecule. Generally, buffers having a pH in a range between about 4 and about 9 can be used, with a pH between about 6 and about 8 desired for certain pH sensitive biomolecules. Generally, the oxidation is carried out at a temperature between about 0 and about 50 degrees Celsius, and preferably at a temperature between about 4 and about 37 degrees Celsius. Depending on the biomolecule, oxidation reactions can be carried out for as short as a few minutes to as long as many days. Commonly, oxidation is complete within 24 hours. Long-term oxidation reactions are preferably performed in the dark to prevent "overoxidation."

Treatment times and temperatures for the oxidation process tend to be inversely related. That is, higher treatment temperatures require relatively shorter treatment times. Time and temperature limitations of the present invention are generally governed by the biological stability of the biomolecules imparted by the oxidation process. Wide latitude may be employed in determining the optimum conditions for a particular system. Such conditions may be determined readily by one skilled in the art by routine experimentation upon examination of the information presented herein.

Subsequent to oxidation, the reaction solution may be stored prior to attachment to a substrate at about 4 degrees Celsius. Typically, the storage stability of the reaction solution at a neutral pH or slightly acidic pH may extend between about one and about fourteen days and sometimes even months when stored in the dark.

The resultant aldehyde moieties interact with sites on a biomaterial surface for covalent attachment of the biomolecules. These biomaterial surface attachment sites comprise amine moieties, which react with aldehyde moieties forming imines.

Another aspect of the invention is a germ free composition obtainable by a method as described above. In one embodiment the germ free composition comprises at least one disinfectant dye selected from the group consisting of methylene blue and related thionine dyes, acridine orange, acridine yellow and related acriflavine (acridine) dyes, proflavine hemisulphate, quinacrine and its derivatives, brilliant green, gentian violet, crystal violet and related triphenyl methane dyes, bis naphthalene dyes such as trypan blue and trypan red, and/or combinations thereof. It is appreciated that any of the listed artificial organic dyes may be used in separate embodiment and/or combinations. It is further anticipated that at least one, such as at least two, such as at least three disinfectant dyes, for example at least four disinfectant dyes, such as at least five disinfectant dyes, such as at least six disinfectant dyes, for example at least seven disinfectant dyes, such as at least eight disinfectant dyes, such as at least nine disinfectant dyes, for example at least ten disinfectant dyes.

In a preferred embodiment of the present invention, the chemical substance(s) may comprise solutions of "Double dye" (methylene blue plus crystal violet) by adding a stock solution containing equal weight percentages of the two dyes. For example, a double dye stock solution of 1% by weigh of each of the dye may be conveniently used. In a particular embodiment the disinfectant dyes are a combination of methylene blue and crystal violet.

Another aspect of the present invention is a germ free composition, comprising colostrum, part or derivatives thereof, comprising at least 80% active native immunoglobulins, such as at least 75% active native immunoglobulins, such as at least 70% active native immunoglobulins, such as at least 65% active native immunoglobulins, such as at least 60% active native immunoglobulins, such as at least 55% active native immunoglobulins, such as at least 50% active native immunoglobulins, such as at least 45% active native immunoglobulins, such as at least 40% active native immunoglobulins, such as at least 35% active native immunoglobulins, such as at least 30% active native immunoglobulins.

The chemical substance(s) may further comprise a reducing agent, such as ascorbic acid in combination with a disinfectant dye, as described elsewhere herein.

The chemical substance(s) may further comprise a cell lysing agent such as a detergent. In yet another aspect the present invention relates to a composition comprising immunoglobulins, part or fragments thereof, wherein said immunoglobulins are synthetically multimerised.

Immunoglobulins come in different varieties known as isotypes or classes. In placental mammals there are five immunoglobulin isotypes known as IgA, IgD, IgE, IgG and IgM, which differ in their biological properties, functional locations and ability to deal with different antigens, as depicted in table 2 below.

TABEL 2

| Immunoglobulins | |
| --- | --- |
| Name | Description |
| IgA | Found in mucosal areas, such as the gut, respiratory tract and urogenital tract, and prevents colonization by pathogens. Also found in saliva, tears, and breast milk. |
| IgD | Functions mainly as an antigen receptor on B cells that have not been exposed to antigens. Its function is less defined than other isotypes. |
| IgE | Binds to allergens and triggers histamine release from mast cells and basophils, and is involved in allergy. Also protects against parasitic worms. |
| IgG | In its four forms, provides the majority of antibody-based immunity against invading pathogens. The only antibody capable of crossing the placenta to give passive immunity to fetus. |
| IgM | Expressed on the surface of B cells and in a secreted form with very high avidity. Eliminates pathogens in the early stages of B cell mediated (humoral) immunity before there is sufficient IgG |

The antibody isotype of a B cell changes during cell development and activation. Immature B cells, which have never been exposed to an antigen, are known as naïve B cells and express only the IgM isotype in a cell surface bound form. B cells begin to express both IgM and IgD when they reach maturity—the co-expression of both these immunoglobulin isotypes renders the B cell 'mature' and ready to respond to antigen. B cell activation follows engagement of the cell bound antibody molecule with an antigen, causing the cell to divide and differentiate into an antibody producing cell called a plasma cell. In this activated form, the B cell starts to produce antibody in a secreted form rather than a membrane-bound form. Some daughter cells of the activated B cells undergo isotype switching, a mechanism that causes the production of antibodies to change from IgM or IgD to the other antibody isotypes, IgE, IgA or IgG, that have defined roles in the immune system.

The immunoglobulins of the present composition are IgG, IgA, IgM, IgE, IgD and/or IgY. In a particular embodiment the immunoglobulins are IgG.

The present invention relates to compositions comprising chemical and/or molecular substances that comprise active sites that are directed toward microorganisms, and wherein said compositions thus have anti-microbial activity. The active sites may for example be the antigen-binding sites on immunoglobins molecules, but may refer to any site on any chemical and or molecular substance that provide contributions to the anti-microbial activity.

The present invention thus relates to compositions comprising chemical and/or molecular substances, wherein each said substance comprise active sites providing contributions to anti-microbial activity, such as at least at leas at least 1 active sites, such as at least 2 active sites, such as at least 2 active sites, such as at least 4 active sites, such as at least 5 active sites, such as at least 6 active sites, such as at least 7 active sites, such as at least 8 active sites, such as at least 9 active sites, such as at least 10 active sites, such as at least 11 active sites, such as at least 12 active sites, such as at least 13 active sites, such as at least 14 active sites, such as at least 15 active sites, such as at least 16 active sites, such as at least 17 active sites, such as at least 18 active sites, such as at least 19 active sites, such as at least 20 active sites, such as at least 25 active sites, such as at least 30 active sites, such as at least 35 active sites, such as at least 40 active sites, such as at least 45 active sites, such as at least 50 active sites, such as at least 55 active sites, such as at least 55 active sites, such as at least 60 active sites, such as at least 65 active sites, such as at least 70 active sites, such as at least 75 active sites, such as at least 80 active sites, such as at least 85 active sites, such as at least 90 active sites, such as at least 9 active sites, such as at least 100 active sites.

Thus, in one embodiment the present invention relates to a germ free composition comprising colostrum, wherein the composition comprises chemical and/or molecular substances with active sites providing contributions to anti-microbial activity.

In another embodiment the present invention relates to a composition comprising synthetically multimerised immunoglobulins, wherein the immunoglobulins comprises active sites providing contributions to anti-microbial activity.

In another embodiment the present invention relates to a germ free composition comprising colostrum enriched with synthetically multimerised immunoglobulins, wherein the composition comprises chemical and/or molecular substances with active sites providing contributions to anti-microbial activity.

The synthetically multimerised immunoglobulins comprise at least 4 active sites contributing to antimicrobial activity.

In a preferred embodiment the immunoglobulin comprised in the product is a purified active native immunoglobulin. The purity of the active native immunoglobulin is preferably at least 10%, such as at least 20%, such as at least 25%, such as at least 30%, such as at least 35%, such as at least 40%, for example at least 45%, such as at least 50%, such as at least 55%, such as at least 60%, such as at least 65%, such as at least 70%, such as at least 75%, for example at least 80%, such as at least 85%, such as at least 90%, such as at least 91%, such as at least 92%, such as at least 93%, for example at least 94%, such as at least 95%, such as at least 96%, for example at least 97%, such as at least 98%, for example at least 99% w/w.

When a purified immunoglobulin is to be administered to a subject instead of milk or colostrum it becomes possible to inactivate or remove pathogenic microorganisms from the immunoglobulin by way of several methods such as sterile filtration including microfiltration and ultrafiltration techniques. Other preferred inactivation treatments are irradiation with UV-light or electromagnetic irradiation. Also pasteurisation is a possible treatment to inactivate pathogenic microorganisms when the product comprises purified immunoglobulins.

According to another aspect of the present invention, the cross-linking comprises the formation of polymerised/multimerised immunoglobulins, parts of immunoglobulins or derivatives of immunoglobulins.

The present invention also relates to a method for producing synthetically multimerised immunoglobulin comprising the steps of
i) providing a starting material
ii) isolating immunoglobulin, part or fragments thereof
iii) multimerising the isolated immunoglobulin of step ii)
iv) obtaining multimerised immunoglobulin or
v) providing a starting material
vi) multimerising components of the starting material of step v)
vii) optionally isolating immunoglobulin, part or fragments thereof
viii) obtaining multimerised immunoglobulin In a preferred embodiment the immunoglobulin, part or fragment thereof of step ii) and/or step iii) is immunoglobulin G, part or fragment thereof.

The said starting material is selected from milk, colostrum, whey, serum, plasma, eggs or any part or derivates thereof. The components and characteristics of colostrum are described elsewhere herein. Colostrum of bovine origin is preferred. In one embodiment the starting material is whey.

Whey or milk plasma is the liquid remaining after milk has been curdled and strained; it is a by-product of the manufacture of cheese or casein and has several commercial uses.

Sweet whey is manufactured during the making of rennet types of hard cheese like Cheddar or Swiss cheese. Acid whey (also known as sour whey) is obtained during the making of acid types of cheese such as cottage cheese.

Whey is a by-product of cheese production; it is one of the components which separates from milk after curdling, when rennet (often a by-product of veal production, which are in turn often fed on whey) or an edible acidic substance is added.

Whey is used to produce ricotta and brown cheeses and many other products for human consumption. It is also an additive in many processed foods, including breads, crackers and commercial pastry, and in animal feed. Whey proteins primarily consist of α-lactalbumin and β-lactoglobulin. Depending on the method of manufacture, whey may also contain glycomacropeptides (GMP).

Whey protein is the name for a collection of globular proteins that can be isolated from massive whey. It is typically a mixture of globinstagers beta-lactoglobulin (~65%), alpha-lactalbumin (~25%), and serum albumin (~8%), which are soluble in their native culture forms, independent of pH. Whey protein has an even higher bioavailability than egg white protein, which is considered the "gold standard" of protein, and has a bioavailability rating of 100. Bioavailability refers to how quickly a substance will be digested and absorbed through the cilia in the small intestine and thus into the blood stream. Preferably the starting material for the production of synthetically multimerised immunoglobulin of the present invention comprises natural colostrum, natural milk, milk concentrate, whey or whey concentrate.

In one embodiment of the present invention, the natural colostrum, natural milk, milk concentrate, whey, whey concentrate or part thereof, originates from bovine, equine, porcine, human, ovine, caprine or cervidae. However, in another embodiment the natural colostrum, natural milk, milk concentrate, whey, whey concentrate or part thereof is of bovine, porcine or human origin. In a preferred embodiment the the natural colostrum, natural milk, milk concentrate, whey, whey concentrate or part thereof is of bovine origin.

In a preferred embodiment, the starting material is sweet whey, in particular bovine sweet whey. However, in another preferred embodiment the starting material is bovine colostrum.

The immunoglobulins of step ii) or step vii) are isolated by chromatography or any other procedure able to isolate immunoglobulins. In a preferred embodiment the chromatography comprises as adsorbent such as protein A, ion exchange adsorbents and/or protein G In one embodiment the multimerisation of step iii) and/or step vi) involves cross-linking of the immunoglobulins of step ii), and/or the components of the starting material of step v) As described elsewhere herein cross-linking agents catalyse the formation of cross-linking that is the covalent chemical bond that link one polymer/multimer chain to another.

In one embodiment of the present invention the cross-linker is selected from EGS (Ethylene glycol bis[succinimidylsuccinate]), Sulfo EGS (Ethylene glycol bis[sulfosuccinimidylsuccinate]), C6-SANH (C6-succinimidyl 4-hydrazinonicotinate acetone hydrazone), SANH (succinimidyl 4-hydrazinonicotinate acetone hydrazone), C6-SFB (C6-succinimidyl 4-formylbenzoate), BSOCOES (Bis[2-(succinimidyloxycarbonyloxy)ethyl]sulfone), DSP (Dithiobis[succinimidyl propionate]), DTSSP (3,3"-Dithiobis[sulfosuccinimidylpropionat]), DTBPD (Dimethyl 3,3'-dithiobispropionimidate•2 HCl), DSS (Disuccinimidyl suberate), BS (Bis[sulfosuccinimidyl]suberate), DMS (Dimethyl Suberimidate•2 HCl), DMP (Dimethyl pimelimidate•2 HCl), DMA (Dimethyl adipimidate•2 HCl), SHTH (Succinimidyl 4-hydrazidoterephthalate hydrochloride), DSG (Disuccinimidyl glutarate), MSA (Methyl N-succinimidyl adipate), DST (Disuccinimidyl tartarate), SFB (Succinimidyl 4-formylbenzoate), DFDNB (1,5-Difluoro-2,4-dinitrobenzene), DSP (Dithiobis[succinimidyl propionate]), DTSSP (3,3"-Dithiobis[sulfosuccinimidylpropionate]), EDC/NHS, glutaraldehyde, dihydroxyacetone, phenyl azide, tyrosinase, transglutaminase and/or periodate.

In another embodiment of the present invention, the cross-linking agent is selected from EDC/NHS or derivatives thereof, glutaraldehyde or derivatives thereof, transglutaminase or derivatives thereof, tyrosinase or derivatives thereof, and/or dihydroxyacetone or derivatives thereof.

In yet other embodiments the cross-linking agent is dihydroxyacetone or derivatives thereof, the cross-linking agent is EDC/NHS or derivatives thereof, the cross-linking agent is glutaraldehyde or derivatives thereof, the cross-linking agent is transglutaminase or derivatives thereof, the cross-linking agent is glutaraldehyde or derivatives thereof, the cross-linking agent is transglutaminase or derivatives thereof, the cross-linking agent is tyrosinase or derivatives thereof.

In a particular embodiment the cross-linking agent is periodate, such as sodium periodate, potassium periodate, lithium periodate and calcium periodate. In a preferred embodiment the cross-linking agent is sodium periodate.

Polymerisation/Multimerisation of Biomolecules with Periodate or Periodate Forming Agents Biomolecules that possess carbon—carbon bonds bearing an amine moiety adjacent to a hydroxyl moiety are oxidizable with periodate. A carbon—carbon bond bearing an amine moiety adjacent to a hydroxyl moiety is known as a 2-aminoalcohol moiety. The 2-aminoalcohol moiety is oxidizable with periodate, which can be provided as periodic acid or salts thereof, such as sodium periodate, potassium periodate, or other alkali metal periodates. Typically, a stoichiometric amount of periodate is used to oxidize the 2-aminoalcohol moiety, although an excess could be used. Oxidation of such biomolecules forms reactive aldehyde moieties within the biomolecules.

The oxidation is carried out in an aqueous solution, preferably an aqueous buffered solution, at a temperature that does not destroy the biological properties of the biomolecule. Generally, buffers having a pH in a range between about 4 and about 9 can be used, with a pH between about 6 and about 8 desired for certain pH sensitive biomolecules. Generally, the oxidation is carried out at a temperature between about 0 and about 50 degrees Celsius, and preferably at a temperature between about 4 and about 37 degrees Celsius. Depending on the biomolecule, oxidation reactions can be carried out for as short as a few minutes to as long as many days. Commonly, oxidation is complete within 24 hours. Long-term oxidation reactions are preferably performed in the dark to prevent "overoxidation."

Treatment times and temperatures for the oxidation process tend to be inversely related. That is, higher treatment temperatures require relatively shorter treatment times. Time and temperature limitations of the present invention are generally governed by the biological stability of the biomolecules imparted by the oxidation process. Wide latitude may be employed in determining the optimum conditions for a particular system. Such conditions may be determined readily by one skilled in the art by routine experimentation upon examination of the information presented herein.

Subsequent to oxidation, the reaction solution may be stored prior to attachment to a substrate at about 4 degrees Celsius. Typically, the storage stability of the reaction solution at a neutral pH or slightly acidic pH may extend between about one and about fourteen days and sometimes even months when stored in the dark.

The resultant aldehyde moieties interact with sites on a biomaterial surface for covalent attachment of the biomolecules. These biomaterial surface attachment sites comprise amine moieties, which react with aldehyde moieties forming imines.

In another embodiment the at least one cross-linking agent is selected from periodate or periodate forming agents. Periodates that are particularly useful are periodates such as sodium periodate, potassium periodate, lithium periodate and calcium periodate. In a preferred embodiment the periodate is sodium periodate.

In yet another aspect the present invention relates to a composition obtainable by the method for producing synthetically multimerised immunoglobulins as disclosed herein. In yet another aspect the present invention relates to a composition comprising germ free colostrum or part thereof or derivative thereof, enriched with immunoglobulins, part or fragments thereof, wherein said immunoglobulins are synthetically multimerised as disclosed in the present invention.

In one embodiment the germ free colostrum is obtained by any method removing microorganisms, such as pasteurisation, heat inactivation, radiation, centrifugation or filtration.

A particular embodiment of the present invention relates to a composition comprising i) a composition comprising germ free colostrum as described in the present invention, part or fragment thereof and ii) synthetically multimerised immunoglobulins, part or fragment thereof.

In another embodiment the synthetically multimerised immunoglobulins are obtained from a starting material such as milk, colostrum, whey, serum, plasma, eggs or any part or derivatives thereof.

In a particular embodiment the starting material is whey.

In another particular embodiment the starting material is colostrum.

A preferred embodiment of the present invention relates to a composition comprising i) a composition comprising germ free colostrum as described in the present invention, part or fragment thereof and ii) synthetically multimerised immunoglobulins, part or fragment thereof as described in the present invention.

Pathogenic Microorganisms

The pathogenic microorganism giving rise to pathogenic infections as described in the uses of the present invention is to be inactivated by the treatment may be selected from the group of: virus, bacteria and parasites.

Enteropathogens adressed by the present invention include but are not limited to enterobacteria, enterococci, corynebacteria, *Salmonella* spp, *Mycobacterium avium* ssp. *paratuberculosis, Brachyspira hyodysenteriae, Lawsonia intracellularis, campylobacter* spp., clostridia, coronavirus, rotavirus, torovirus, calicivirus, astrovirus, canine parvovirus, coccidia and cryptosporidia.

In one embodiment, the enteropathogens in cattle addressed by the present invention include but are not limited to enteropathogenic *E. coli* (VTECT/ETEC), *Salmonella* spp, *Yersinia* spp., including *Yersinia enterocolitica, Mycobacterium avium* ssp. *paratuberculosis, Coxiella burnetti*, the causative agent of Q fever, rotavirus, coronavirus, calicivirus, bovine virus diarrhoea virus, bovine herpes virus, rinderpest virus, coccidia, and cryptosporidia.

In another embodiment the enteropathogens in pigs addressed by the present invention include but are not limited to *Salmonella* spp, *Lawsonia intracellularis, Campylobacter* spp, Enteropathogenic *E. coli* (VTECT/ETEC), *Brachyspira* spp including *Brachyspira hyodysenteria, Clostridium* spp, rotavirus, sappovirus, norovirus, and coronavirus.

In yet another embodiment, the enteropathogens in humans addressed by the present invention may comprise but is not limited to *Salmonella* spp, *Camphylobacter* spp., Norovirus, rotavirus, *Vibrio* spp. including *Vibrio cholera, Shigella* spp., *Helicobacter* spp., coccidia and cryptosporidia.

The pathogenic microorganism to be inactivated by the treatment may be selected from the group of: virus, bacteria and parasites.

Particularly relevant bacteria are: *Mycobacterium avium* ssp. *paratuberculosis, Salmonella* spp., *Listeria monocytogenes, Escherichia coli, Campylobacter* spp., *Streptococcus* spp.

Preferably the immunoglobulins may be isolated and purified from milk, colostrum, whey, blood, serum, plasma, egg yolk, egg white or any derivatives or fractions of such raw materials and preferably the immunoglobulin is originating from farm production animals such as cows, goats, sheep, fowl, pigs, chickens, hens, fish and shell fish.

Further, in another aspect of the invention, the new born mammal, such as the new born calf, is separated from the dam before it reaches the udder and starts to suck colostrum from the dam followed by feeding the new born mammal with a colostrum, colostrum replacer, colostrum supplement or a combination of these treated to inactivate or remove pathogenic microorganisms according to the invention.

An Antimicrobial Composition for Administration to a Newborn Farm Production Animal The present invention further provides antimicrobial substances, such as IgG or IgA derivatives, which comprises polymerised monomeric substances which have been chemically and covalently linked. These polymerised substances exhibits high avidity, however many of the difficulties and costs associated with the isolation, of e.g. SIgA's, on a large scale or preparation of genetically engineered organisms giving narrow antigen binding specificities, have been avoided.

Such substances, e.g. IgG derivatives, may yield more clinically effective and commercially viable products for passive immunisation of skin, skin lesions, surgical wounds and mucosal surfaces and which enhances the positive effect of the natural antibodies and quite remarkably.

In an embodiment of the present invention a therapeutic formulation may be provided comprising at least two of said antimicrobial substances that are suitable for passive immunisation and enhanced anti-microbial activity at skin and mucosal surfaces and especially formulations that have enhanced stability towards gastrointestinal secretions such as acid and proteases.

In another embodiment of the present invention methods for the preparation of said antimicrobial substances that may be compatible with therapeutic use, with minimal introduction of foreign matter and devoid of any toxic substances arising from many prior art antibody derivatisation steps may be provided.

The emergence of bacterial strains resistant to multiple antibiotics and the progresses made in antibody engineering give other strong arguments to prompt implementation of passive immunization. Mucosal delivery may provide shorter-term protection as compared with relatively long-lasting parenteral delivery, but may have several advantages when human administration is concerned.

For gastrointestinal treatment, the antibody molecules can be given in combination with biologic fluids and blockers of gastric acid secretions and proteases capable to protect the protein from rapid degradation. For treatment of the upper airways, antibody molecules can be delivered by nose drops or spray. Safety concerns may be reduced with mucosally delivered antibody, as it reaches surfaces constantly exposed to foreign materials. Immunity against non-human molecules may be expected to develop after long-term use only.

Upon mucosal administration, problems associated with blood products and handling may be reduced, and adverse reactions including thromboembolic events, renal failure, aseptic meningitis, are unlikely to occur.

Another advantage may lie in the intrinsic capability of the antibody to neutralize the pathogen at a very early stage of infection, or even prior to the initiation of the infection. The amount and pace at which the antibody may be delivered to remain active might depend on the infectious status, the nature of the mucosal surface, and the antibody isotype.

In an embodiment of the present invention IgG derivatives may be polymerised, such as controlled polymers of non-denatured immunoglobulin G, giving enhanced inhibition of microbial activity at skin and mucosal surfaces.

In a preferred embodiment of the present invention the polymerisation may be based on the oxidation of carbohydrate moieties of the immunoglobulin molecules with periodate followed by coupling/reaction with amino groups present on the immunoglobulin molecules themselves (homopolymerisation) or amino groups present on other proteins present optionally optionally in the presence of lyotropic salts or other water structuring substances such as polyethylene glycol.

In a preferred method for preparation of a polymerised immunoglobulin composition said method comprise the steps of:
  i) providing an aqueous solution comprising carbohydrate conjugated immunoglobulins
  ii) reacting said solution with periodate to oxidise said carbohydrate moieties to comprise active aldehyde groups
  iii) optionally adjusting pH iv) allowing the oxidised carbohydrate moieties to react with amino groups on neighbouring immunoglobulin molecules and/or other proteins or polymers present in the solution In a preferred embodiment of the method the aqueous solution contains a highly purified immunoglobulin. In a preferred embodiment of the method the aqueous solutions is a complex mixture of proteins and other components such as crude colostrum, colostral whey, whey, whey concentrates, blood, plasma, serum or egg yolk.

In a preferred embodiment said complex mixture is separated into a high molecular weight fraction comprising the polymerised immunoglobulin and a low molecular weight fraction comprising other substances.

In a preferred method the high molecular weight fraction comprise at least 70%, such as at least 80%, such as at least 90% on a dry matter basis of polymerised molecules having a molecular weight higher than 150.000 Dalton In a preferred method the separation is performed by means of membrane filtration.

In a preferred method the separation is performed by selective precipitation of the high molecular weight fraction followed by decantation, centrifugation or filtration In a preferred method the selective precipitation is achieved by addition of lyotropic salts, water structuring polymers (such as polyethylene glycol) or organic solvent.

In a preferred embodiment of the present invention the polymerisation of the antimicrobial substances may be performed by chemical reaction wherein selected groups of the antimicrobial substances may be activated whereby it becomes reactive towards other, preferably similar activated antimicrobial substances and forming a chemical covalent bond. Preferably, the polymerisation of the antimicrobial substances may be performed substantially without contamination of any host antigens that may evoke allergic or other adverse reaction products.

In a preferred embodiment the antimicrobial substances (ie. the composition comprising synthetically multimerised immunoglobulins) comprise polymers comprising one or more covalently coupled antimicrobial peptide(s) such as oligopeptides, polypeptides, or peptidomimetics that kill (i.e., bacteriocidal) or inhibit the growth of (i.e., bacteriostatic) microorganisms including bacteria, yeast, fungi, mycoplasma, viruses or virus infected cells, and/or protozoa including linear peptides that form an $\alpha$-helical structure in membranes or peptides that form $\beta$-sheet structures optionally stabilized with disulfide bridges in membranes. Representative antimicrobial peptides include, but are not limited to, cathelicidins, defensisn, dermeidin, and more specifically magainin 2, protegrin, protegrin-1, melittin, 11-37, dermaseptin 01, cecropin, caerin, ovispirin, and alamethicin. Naturally occurring antimicrobial peptides include peptides from vertebrates and nonvertebrates, including plants, humans, fungi, microbes, and insects.

Proteolytic Stability Properties of the Compositions of the Present Invention

Protelytic stability is used to describe the resistance of a given protein toward proteolysis, i.e. hydrolysis of the peptide (amide) bonds in the protein or peptide. In particular, proteolytic stability refers to the resistance toward the action of proteolytic enzymes, also known as proteases, i.e. enzymes that catalyzes the hydrolysis of the protein or peptide.

One embodiment of the present invention relates to a germ free composition comprising colostrum, wherein said composition has increased stability towards hydrolysis by proteases, as compared to a composition containing raw colostrum. In another embodiment the present invention relates to a composition comprising synthetically multimerised immunoglobins, wherein said composition has increased stability towards hydrolysis by proteases, as compared to a composition containing native immunoglobins. In yet another embodiment the present invention relates to a germ free composition comprising colostrum enriched with synthetically multimerised immunoglobins, wherein said composition has increased stability towards hydrolysis by proteases, as compared to a composition containing raw colostrum enriched with native immunoglobins.

According to another aspect of the present invention, the cross-linking comprises the formation of a polymerised/multimerised composition comprising colostrum parts of colostrum or derivatives enriched with immunoglobulins, parts of immunoglobulins or derivatives of immunoglobulins. In yet another aspect of the present invention, said composition is enriched with immunoglobulins, parts of immunoglobulins or derivatives of immunoglobulins, wherein the said immunoglobulins have been synthetically multimerised.

Methods and Uses

The methods and uses of the compositions of the present invention that relate to combating pathogenic infections and/or for providing passive immunisation to a subject.

The subjects of the present methods and uses are selected from cattle, pig, horse, sheep, goat, fish, camel, hens, chicken, duck, geese, llamas, farmed deer, bison and humans. Cattle are herein also referred to as cows. In a preferred embodiment of the invention the subjects are selected from the group consisting of cows, pigs, hens, chicken, fish and humans. A particular embodiment is cows. However, also humans represent another subject of particular relevance in the present invention, as does hens and chicken, but also fish, and in a particular embodiment also pigs.

The subjects may be of any age for example newborn, less than 24 hrs old, in particular cows or piglets.

Methods and uses for preventing, ameliorating and/or treating pathogenic infections and for passive immunisation In one aspect the present invention relates to a method for preventing, ameliorating and/or treating pathogenic infections comprising administration of the compositions of the present invention. Thus, the present invention relates to a method for preventing, ameliorating and/or treating pathogenic infections comprising administration of a germ free composition comprising colostrum, administrating a composition comprising synthetically multimerised immunoglobulins; and/or administrating a germ free composition comprising colostrum, enriched with a synthetically multimerised immoglobulins, in a therapeutically effective amount to a subject in need thereof.

In another aspect the present invention relates to a pharmaceutical composition for preventing, ameliorating and/or treating pathogenic infections comprising the compositions of the present invention. Therefore, the present invention relates to a pharmaceutical composition for preventing, ameliorating and/or treating pathogenic infections comprising the germ free composition comprising colostrum, the composition comprising synthetically multimerised immunoglobulins; and/or the germ free composition comprising colostrum, enriched with a synthetically multimerised immunoglobulins.

In a further aspect the present invention pertains to use of the compositions of the present invention for the manufacture of a medicament for the prevention, amelioration and/or treatment of pathogenic infection. Thus, it is within the scope that to use the germ free composition comprising colostrum, the composition comprising synthetically multimerised immunoglobulins; and/or the germ free composition comprising colostrum, enriched with a synthetically multimerised immunoglobulins for the manufacture of a medicament for the prevention, amelioration and/or treatment of pathogenic infection.

In yet another aspect the present invention pertains to compositions of the present invention for the prevention, amelioration and/or treatment of pathogenic infection. Consequently, the germ free composition comprising colostrum, the composition comprising synthetically multimerised immunoglobulins; and/or the germ free composition comprising colostrum, enriched with a synthetically multimerised immunoglobulins is for the prevention, amelioration and/or treatment of pathogenic infection.

A key component of the survival and health of calves is colostrum feeding in the first 24 hours of life. Veterinarians and farmers have known for more than one hundred years the importance of colostrum feeding in maintaining the health of young animals, including calves, foals, kids, lambs, pigs, cats and dogs. It has been estimated that the absorption of IgG in the first 24 hours of life determines the degree of acquisition of passive immunity and subsequent resistance to disease. Nearly 11% of dairy calves in USA die prior to weaning, and the mortality can for a majority of cases be attributed to inadequate colostral IgG intake and that estimated 40% of dairy heifer calves have failure of passive transfer at 24 hours of age. The amount of IgG absorbed by the calf is determined by many factors, including the concentration of IgG in colostrum, feeding practices of the farm and metabolic state of the animal. Colostrum is widely variable in IgG concentration. The presence of contaminants in colostrum and milk adds a degree of risk to neonatal feeding. Colostrum and milk is recognized as a vector for transmission of a number of disease causing organisms, including the widespread *Mycobacterium avium* subsp. *paratuberculosis* (in short: *Mycobacterium paratuberculosis*) causing Johne's disease in cattle. Farms with significant Johne's infestation often have inadequate supplies of colostrum to feed to their newborn calves. Consequently, farmers are forced to rely on feeding milk replacers and using large amounts of antibiotics to keep the animal alive until its own active immune system can protect it.

*Mycobacterium paratuberculosis* is the agent of a chronic, fatal, granulomatous enterocolitis in ruminants also called *paratuberculosis* or Johne's disease. Johne's disease is a chronic, debilitating intestinal disorder in cattle characterized by diarrhoea, reduced feed intake, weight loss and death. Calves acquire the infection in the first months of life through oral uptake of colostrum, milk or feces of infected cows. They either successfully clear the infection or become subclinically infected for life. The subclinically infected animals shed the bacteria in their feces intermittently or continuously from an age of approximately two years onward. After an incubation period of four to five years, a proportion of the subclinically infected animals develop an incurable progressive form of protein-losing enteropathy with chronic diarrhoea that is ultimately fatal.

In a particular embodiment the subject is a newborn calf (cow) less than 24 hrs old. Such a subject can benefit from the germ free composition, comprising colostrum, the composition comprising synthetically multimerised immunoglobulins; and/or the germ free composition comprising colostrum, enriched with a synthetically multimerised immunoglobulins is for the prevention, amelioration and/or treatment of pathogenic infection. The calf's mother may be separated from the newborn calf in order for the newborn cow not to be infected by the mother, for example pathogenic infections such as *E. coli* (VTECT/ETEC), *Salmonella* spp, *Yersinia* spp., including *Yersinia enterocolitica*, *Mycobacterium avium* ssp. *paratuberculosis, Coxiella burnetti*, the causative agent of Q fever, rotavirus, coronavirus, calicivirus, bovine virus diarrhoea virus, bovine herpes virus, rinderpest virus, coccidia, and cryptosporidia, in particular *Mycobacterium avium* ssp. *paratuberculosis*, rotavirus, bovine virus diarrhoea virus. In a particular embodiment a newborn calf (cow) less than 24 hrs old can benefit from the germ free composition, comprising colostrum, the composition comprising synthetically multimerised immunoglobulins; and/or the germ free composition comprising colostrum, enriched with synthetically multimerised immunoglobulins is for the prevention, amelioration and/or treatment of *Mycobacterium avium* ssp. *Paratuberculosis*.

A newborn calf ingests in the range of 1-3 liter of colostrum per 24 hrs corresponding to 1-3 grams immunoglobulin per kg body weight. Thus, a newborn animal separated from its mother needs to ingest an amount of germ free composition comprising colostrum equivalent to 1-3 liters of natural colostrum. However, the amount of colostrum to feed a calf depends on several factors—including the amount of antibody (or immunoglobulin) in the colostrum, the body weight of the calf, the age of the calf at first feeding, and several other factors. In order to calculate the amount (or mass) of IgG that a calf needs, several assumptions may be made, based on existing research data (see list below). The goal is for the calf to obtain a minimum of 10 grams of IgG per liter of serum. A calf's plasma volume at 24 hours of age is approximately 9% of its body weight. To achieve 10 g/L, a newborn calf that weighs 40 kg (about 88 lbs.) must consume 36 grams of IgG from colostrum or a supplement by 24 hours of age. However, IgG is not absorbed with 100% efficiency. Research data suggest the efficiency is closer to 35% (the other 65-70% equilibrates with other body pools or is not absorbed at all). So, to achieve 10 g/L, the calf must consume 103 grams of IgG (36 grams/35%) by 24 hours. If a margin of safety is included in the calculations (achieving a plasma IgG concentration of 15 grams of IgG per liter), the calf needs to consume 154 grams of IgG.

Estimated Colostrum Required by a 40 kq Calf to Achieve Minimum Plasma IgG Concentration.

| | |
|---|---|
| Calf body weight | 40 kg |
| Plasma volume (9% of BW) | 3.6 liters |
| Minimum Plasma concentration | 10 g/L |
| Apparent efficiency of absorption | 35% |
| Required IgG intake | 103 grams |
| Colostral concentration | 50 g/L |
| Required colostrum amount to feed | 2.1 L |

A newborn calf receiving colostrum from its mother may in one embodiment benefit from the intake of the composition comprising synthetically multimerised immunoglobulins of the present invention corresponding to at least 20 gram immunoglobulin, such as at least 30 gram immunoglobulin, such as at least 40 gram immunoglobulin, such as at least 50 gram immunoglobulin, such as at least 75 gram immunoglobulin, such as at least 100 gram immunoglobulin, such as at least 125 gram immunoglobulin, within the first 36 hours from birth.

A newborn calf less than 24 hrs old separated from its mother may benefit from receiving the germ free composition comprising colostrum, enriched with a synthetically multimerised immoglobulins according to the present invention in order to prevent, ameliorate or treat pathogenic infections, in particular *Mycobacterium avium* ssp. *Paratuberculosis*.

The compositions of the present invention are used for passive immunisation of a subject. In contrast to for example vaccines, passive immunization can deliver protective levels of antibodies directly to the susceptible mucosal site where most infections begin. Passive protection by transfer of antibody from maternal origin for example through colostrum represents in many species including humans an efficacious and specific mechanism to prevent mucosal infection in newborns lacking a fully matured immune system. This takes place by ingestion of breast milk containing immunoglobulins induced by natural exposure of the maternal immune system to environmental microbes.

Thus, within the scope of the present invention is a method for passive immunisation of a subject comprising the step of administering the compositions of the present invention in an effective amount to a subject. The germ free composition comprising colostrum, the composition comprising synthetically multimerised immunoglobulins; and/or the germ free composition comprising colostrum, enriched with a synthetically multimerised immoglobulins is administered in an effective amount to a subject in accordance with the method for passive immunisation.

A further aspect relates to use of the compositions of the present invention for the manufacture of a medicament for passive immunisation of a subject. Thus, the germ free composition comprising colostrum, the composition comprising synthetically multimerised immunoglobulins; and/or the germ free composition comprising colostrum, enriched with a synthetically multimerised immoglobulins may be used for the manufacture of a medicament for passive immunisation of a subject. Similarly, one aspect relates to compositions of the present invention for passive immunisation. Thus, the germ free composition comprising colostrum, the composition comprising synthetically multimerised immunoglobulins; and/or the germ free composition comprising colostrum, enriched with a synthetically multimerised immoglobulins for passive immunisation is within the scope of the present invention. As are aspects relating to pharmaceutical compositions for preventing, ameliorating and/or for passive immunisation comprising the compositions, such as the germ free composition comprising colostrum, the composition comprising synthetically multimerised immunoglobulins; and/or the germ free composition comprising colostrum, enriched with a synthetically multimerised immoglobulins.

The subjects of the present invention may in particular embodiments be a cow of for example a pig or a human, wherein the subject is selected from a newborn subject, 6-12 hours old subject, 12-18 hours old subject 18-24 hour old subject and/or subjects older than 24 hours.

Such a newborn calf may receive the germ free composition comprising colostrum, enriched with immunoglobulins of the present invention such that the amount of immunoglobulins of the present invention corresponds to at least 20 gram immunoglobulin, such as at least 30 gram immunoglobulin, such as at least 40 gram immunoglobulin, such as at least 50 gram immunoglobulin, such as at least 75 gram immunoglobulin, such as at least 100 gram immunoglobulin, such as at least 125 gram within the first 36 hours from birth. The part of the germ free composition comprising colostrum, enriched with immunoglobulins of the present invention that is constituted by the germ free composition comprising colostrum should be administered in an amount of germ free colostrum corresponding to 1-3 liter of colostrum per 24 hrs corresponding 1-3 gram immunoglobulin per kg body weight.

One embodiment of the present uses and methods for prevention, amelioration and/or treatment of pathogenic infection are infections causing diarrhoea also known as traveller's disease. The subjects that may in particular benefit from the composition comprising the synthetically multimerised immunoglobulins of the present invention for prevention, amelioration and/or treatment of a pathogenic infection causing diarrhoea are humans of any age, such as newborn, children, adults and/or elderly persons. Humans should receive in the range of 1-25 mg immunoglobulin per kg body weight, such as 10-20 mg immunoglobulin per kg body weight, such as 1-10 mg immunoglobulin per kg body weight, such as 10-20 mg immunoglobulin per kg body weight, such as 1-5 mg immunoglobulin per kg body weight, such as 1-3 mg of immunoglobulin of the present invention per kg body weight, such as at least 20 mgram immunoglobulin, such as at least 30 mgram immunoglobulin, such as at least 40 mgram immunoglobulin, such as at least 50 mgram immunoglobulin, such as at least 75 gram immunoglobulin, such as at least 100 mgram immunoglobulin, such as at least 125 mgram, or at least 1-3 mg immunoglobulin of the present invention per kg body weight. The preferred rout of administration is by oral intake.

Another embodiment of the present uses and methods for prevention, amelioration and/or treatment of pathogenic infection in animal subjects, wherein the infections causes diarrhoea. The animals may be any of the animals selected from cattle, pig, horse, sheep, goat, fish, camel, hens, chicken, duck, geese, llamas, farmed deer or bison of any age and sex. In particular embodiments the subject is a cow, pig, chicken, hen or horses. In a preferred embodiment the subject is a cow. In particular embodiments the subject is a newborn animal less than 24 hours old, such as 6-12 hours old subject, 12-18 hours old subject 18-24 hour old subject.

As described elsewhere herein the present uses and methods for prevention, amelioration and/or treatment of pathogenic infection in animal subjects, wherein the infections causes paratubercolosis. The animals may be any of the animals selected from cattle, pig, horse, sheep, goat, fish, camel, hens, chicken, duck, geese, llamas, farmed deer or bison of any age and sex. In particular embodiments the subject is a cow, pig, chicken, hen or horses. In a preferred embodiment the subject is a cow. In particular embodiments the subject is a newborn animal less than 24 hours old, however older animals may benefit from the composition comprising synthetically multimerised immunoglobulins of the present invention.

Wounds and Skin HIV and AIDS

In one aspect the present invention relates to a method for preventing, ameliorating and/or treating infections in subjects suffering from diseases suppressing the immune system, wherein the method comprises the step of administering a pharmaceutically effective amount of the composition comprising synthetically multimerised immunoglobulins to a subject in need thereof.

In another aspect the present invention relates to a pharmaceutical composition for preventing, ameliorating and/or treating infections in subjects suffering from diseases suppressing the immune system, wherein the pharmaceutical composition comprises the composition comprising synthetically multimerised immunoglobulins.

In a further aspect the present invention pertains to use of the compositions of the present invention for the manufacture of a medicament for the prevention, amelioration and/or treatment of infections in subjects suffering from diseases suppressing the immune system. Thus, it is within the scope of the present invention to use the composition comprising synthetically multimerised immunoglobulins for the manufacture of a medicament for the prevention, amelioration and/or treatment of infections in subjects suffering from diseases suppressing the immune system.

In yet another aspect the present invention pertains to compositions of the present invention for the prevention, amelioration and/or treatment of infections in subjects suffering from diseases suppressing the immune system. Consequently, the composition comprising synthetically multimerised immunoglobulins is for the prevention, amelioration and/or treatment of infections in subjects suffering from diseases suppressing the immune system.

The subjects that suffer from diseases suppressing the immune system are for example human beings of any age suffering from AIDS and/or cancer.

In yet other aspects the composition comprising synthetically multimerised immunoglobulin may be used in methods for preventing, ameliorating and/or treating wounds, particularly in the skin. Therefore, the present invention relates to a method for preventing, ameliorating and/or treating wounds, said method comprising the step of administering a pharmaceutically effective amount of the composition comprising synthetically multimerised immunoglobulins to a subject in need thereof.

In another aspect the present invention relates to a pharmaceutical composition for preventing, ameliorating and/or treating wounds comprising the composition comprising synthetically multimerised immunoglobulins.

In a further aspect the present invention pertains to use of the compositions of the present invention for the manufacture of a medicament for the prevention, amelioration and/or treatment of wounds. Thus, it is within the scope of the present invention to use the composition comprising synthetically multimerised immunoglobulins for the manufacture of a medicament for the prevention, amelioration and/or treatment of wounds.

In yet another aspect the present invention pertains to compositions of the present invention for the prevention, amelioration and/or treatment of wounds. Consequently, the composition comprising synthetically multimerised immunoglobulins is for the prevention, amelioration and/or treatment of wounds.

In yet other aspects the composition comprising synthetically multimerised immunoglobulin may be used in methods for preventing, ameliorating and/or treating skin diseases. Therefore, the present invention relates to a method for preventing, ameliorating and/or treating skin diseases, said method comprising the step of administering a pharmaceutically effective amount of the composition comprising synthetically multimerised immunoglobulins to a subject in need thereof.

In another aspect the present invention relates to a pharmaceutical composition for preventing, ameliorating and/or treating skin diseases, wherein the pharmaceutical composition comprises the composition comprising synthetically multimerised immunoglobulins.

In a further aspect the present invention pertains to use of the compositions of the present invention for the manufacture of a medicament for the prevention, amelioration and/or treatment of skin diseases. Thus, it is within the scope of the present invention to use the composition comprising synthetically multimerised immunoglobulins for the manufacture of a medicament for the prevention, amelioration and/or treatment of skin diseases.

In yet another aspect the present invention pertains to compositions of the present invention for the prevention, amelioration and/or treatment of skin diseases. Consequently, the composition comprising synthetically multimerised immunoglobulins is for the prevention, amelioration and/or treatment of skin diseases.

In one embodiment, the present invention comprises a pharmaceutical composition and/or compositions for the treatment of skin diseases. For example one aspect relates to a pharmaceutical composition comprising the composition as described herein. In a preferred embodiment, the present invention comprises a pharmaceutical composition further comprising a pharmaceutically and/or physiologically acceptable carrier for the treatment of skin diseases.

A carrier may facilitate the transport of the ingredients of said composition to the site of action, e.g. covalently bound either directly or via a chemical linker. Effective carriers include proteins such as albumins, and/or peptides and polysaccharides such as aminodextran. A carrier may also transport the ingredients of said composition noncovalently bound or by encapsulation, such as within a liposome vesicle or other bio-vesicles.

The skin diseases that can be treated by the composition and/or pharmaceutical composition of the present invention is selected from the group consisting of solar eczema, eczemas of unknown aetiology, rashes, itchy skin conditions, irritated redness, ichtyosis, vitiligo, psoriasis, wounds, postoperative wounds, sores, diabetic sores, lip sores, cracked lips, skin conditions caused by bacteria, skin conditions caused by viruses, skin cancer, acne, impetigo, scabies, sunburn, warts, fifth disease, tinea, herpes, ulcers, pruritus, skin diseases due to absorption of compounds through the skin, bed sore, epidermolysis bullosis, blepharitis, atopic dermatitis, cold sores and boil. It is within the scope of the present invention that any of the listed skin conditions form each their separate embodiment, thus, the skin disease of the present invention is any of solar eczema, eczemas of unknown aetiology, rashes, itchy skin conditions, irritated redness, ichtyosis, vitiligo, psoriasis, wounds, postoperative wounds, sores, diabetic sores, lip sores, cracked lips, skin conditions caused by bacteria, skin conditions caused by viruses, skin cancer, acne, impetigo, scabies, sunburn, warts, fifth disease, tinea, herpes, ulcers, pruritus, skin diseases due to absorption of compounds through the skin, bed sore, epidermolysis bullosis, blepharitis, atopic dermatitis, cold sores or boil.

Eczema, also known as eczematous dermatitis, including rashes, itchy skin conditions, cracks and irritated redness are all conditions characterized by inflammation of the upper layers of the skin. Symptoms include skin edema, itching and dryness, crusting, flaking, blistering, cracking, oozing, and/or even bleeding.

Sores are sites of delayed healing characterized by loss of integrity in the involved area. Sores may be caused by, or accompanied by infection by bacteria fungus and/or viruses. One example is bed sores.

Skin conditions caused by viruses comprises skin conditions such as cold sores which are small, painful, fluid-filled blisters or sores that appear on the lips, mouth, or nose that are caused by a virus. Skin conditions caused by virus are also herpes which is caused by herpes simplex virus. Both strains of Herpes Simplex Virus (HSV-1 and HSV-2) cause the disease. Most common is "oral herpes", causing sores in the face and around the mouth. The second most common disease caused by HSV infects the genitalia, and is known as "herpes". But also other disorders such as herpetic whitlow, herpes gladiatorum, ocular herpes (keratitis), cerebral herpes infection encephalitis, Mollaret's meningitis, neonatal herpes, and possibly Bell's palsy are caused by herpes simplex viruses Ichtyosis, of which ichtyosis vulgaris by far is the most common type, is usually an inherited skin disease although an acquired type of ichtyosis also exists. Ichtyosis is characterized by causing dry, scaly skin. Symptoms are not very severe, usually mild itching and faint scaling of the skin.

Vitiligo is an inherited chronic skin disease characterized by loss of pigment. The symptoms include white patches on the skin and purple and/or golden brown patches on mucous membranes and around the eyes, nostrils and mouth.

Psoriasis is a chronic hyperproliferative inflammatory skin disease. The symptoms are the appearance of red scaly patches of inflammation and excessive skin production, known as psoriatic plaques, especially on elbows and knees. The patches tend to take a silvery-white appearance as skin accumulates at the site of the plaque formation.

Boil is a skin disease caused by the infection of hair follicles, thus resulting in the localized accumulation of pus and dead tissue.

The skin disease which can be treated by the composition and/or pharmaceutical composition of the present invention is selected from the group consisting of solar eczema, eczemas of unknown aetiology, rashes, itchy skin conditions, irritated redness, psoriasis, wounds, postoperative wounds, sores, diabetic sores, lip sores, cracked lips, skin conditions caused by bacteria, skin conditions caused by viruses, acne, sunburn, warts, fifth disease, tinea, herpes, ulcers, pruritus, bed sore and cold sores.

In another embodiment the skin disease which can be treated by the composition and/or pharmaceutical composition of the present invention is selected from the group consisting of eczemas of unknown aetiology, rashes, itchy skin conditions, irritated redness, psoriasis, wounds, postoperative wounds, sores, diabetic sores, skin conditions caused by bacteria, skin conditions caused by viruses, acne, herpes, pruritus and bed sore.

In preferred embodiments the compositions of the present invention is used for the treatment of itchy skin conditions, wounds, sores, eczemas and/or psoriasis. In an especially preferred embodiment the compositions of the present invention is used for the treatment of psoriasis.

The present invention consequently relates to the treatment of any of the skin conditions listed herein comprising administration of the composition of the present invention in a therapeutically effective amount to an animal in need thereof. Similarly, the composition may be used to treat a skin condition in an animal. The term 'animal' as used herein may be defined to include human, domestic or agricultural (cats, dogs, cows, sheep, horses, pigs, etc.) or test species such as mouse, rat, rabbit etc.

One aspect of the present invention relates to the use of the composition of the present invention for the manufacture of a medicament. In analogy, another aspect of the invention relates to use of the composition as a medicament. Furthermore the present invention also relates to a method of treatment of skin conditions comprising administration of the composition of the present invention in a therapeutically effective amount to an animal in need thereof.

For treatment or uses in relation to skin diseases it is appreciated that the composition is used as an agent for topical application. Such an agent for topical application may be in the form of a gel, cream, lotion, ointment, shampoo, mask or similar forms, as exemplified in the examples.

Milk replacer Milk replacers are intended to replace whole milk and to thus provide an economic alternative to whole milk in the raising of the young animal. It is well known that in the early stages of life for a mammal, milk of the dam is the ideal source of nutrition. Unfortunately for many young mammals, whether by tragedy or by economic necessity, as in the case of animals whose milk is commercially valuable, milk of the dam is not always available. In these instances, the use of a milk replacing composition is required.

There exist many formulations for foodstuffs for neo-natal animals that incorporate dried milk products and vitamin and mineral supplements. The common feature of these compositions is that they derive most of their protein content from a milk source ingredient such as skim milk, buttermilk, whole whey, delactosed whey, casein, milk albumin, and/or whey protein concentrate. Some milk replacers include, as ingredients, dried milk, dried whey, dried whey protein concentrate, dextrose, and various vitamins and minerals. Milk source ingredients are used extensively in traditional milk replacers because the existing health data relating to young mammals fed milk replacer diets based on non-milk source ingredients is poor. That is, animals fed with these milk replacers having protein sources other than milk proteins are known to suffer from protein deficiencies that can potentially result in debilitating illnesses. This suggests that only milk-based milk replacers can be used to obtain a healthy young animal.

In one aspect, the present invention relates to a milk replacer comprising a germ free composition comprising colostrum. In another aspect, the present invention relates to a milk replacer comprising a germ free composition comprising colostrum enriched with synthetically multimerised immunoglobulins. Another aspect relates to the use of the compositions of the present invention as a milk replacer for a subject, wherein the subject in one embodiment is a calf not more than 1-3 months old and in another embodiment the subject is a pig not more than 4-6 weeks old In a preferred embodiment the subject is a human not more than 2-3 years old.

Food Supplement

A food supplement, also known as dietary supplement or nutritional supplement, is a preparation intended to supply nutrients, such as vitamins, minerals, fatty acids or amino acids, that are missing or are not consumed in sufficient quantity in a subject's diet. "Food supplement" is in one aspect a preparation or formulation which is added to or otherwise included in a subjects normal diet, and is present in addition to the normal diet. Thus, for example, a food supplement of the present invention can be:
 (i) in the form of a liquid or solid, e.g., powder or as individual dosage units such as tablets or the like to be added to food or drinks, or taken with them,
 (ii) added to a foodstuff or fodder during its preparation, such as added to powdered milk feed, added to liquids including milk and colostrum The present invention relates to a food supplement and, in particular, to a food supplement for promoting the functioning of the immune system, such as providing compositions comprising components for enhancing the function of the immune system. In one aspect the present invention relates to such a food supplement comprising a composition comprising synthetically multimerised immunoglobulins. In another aspect the present invention relates to a food supplement comprising a germ free composition comprising colostrum enriched with synthetically multimerised immoglobulins. Another aspect relates to the use of the compositions of the present invention as a food supplements for a subject. Embodiments include subjects wherein the subject are selected from cattle, cows, pig, horse, sheep, goat, fish, camel, hens, chicken, duck, geese, llamas, farmed deer, bison and humans. A particular embodiment is cows. However, also humans represent another subject of particular relevance in the present invention, as does hens and chicken, but also fish, and in a particular embodiment also pigs.

Growth Promoters

Growth promotion in animals, particularly domestic animals, has in the past been achieved by the addition of catabolic steroidal substances such as oestrogen to animal feed, but also other steroids have benn used. Recently, this practice has fallen into disfavour, as unacceptably high amounts of the steroids accumulate in animal tissues.

It has further been proposed to promote animal growth using various digestive enzymes as feed additives. These enzymes help to break down crude feed material in the intestines, thereby making increased amounts of nutrient materials available for adsorption for a given food ration, over that available under normal digestive conditions. The incorporation of enzymes into feed has the disadvantage that the enzymes are often denatured and inactivated on passage through the stomach or rumen, where extremes of pH are encountered.

Another wide-spread practice is the incorporation of antibiotics into animal feed. This helps to control opportunistic bacterial infection, creating overall better health of stock with consequent weight gain. Antimicrobial growth promoters (AGPs) are antibiotics added to the feed of food animals to enhance their growth rate and production performance. The mechanism by which AGPs work is not clear. The effect on growth may be due to a combination of both fewer normal intestinal flora and fewer harmful bacteria. The class of antimicrobial drugs used and the animal species involved may determine the relative importance of each mechanism.

In one aspect the present invention relates to an antimicrobial growth promoter comprising a composition comprising synthetically multimerised immunoglobulins. In another aspect the present invention relates to an antimicrobial growth promoter comprising a germ free composition comprising colostrum enriched with synthetically multimerised immoglobulins. Another aspect relates to the use of the compositions of the present invention as a growth promoters for a subject. Embodiments include subjects wherein the subject are selected from cattle, cows, pig, horse, sheep, goat, fish, camel, hens, chicken, duck, geese, llamas, farmed deer, bison and humans. A particular embodiment is cows. However, also humans represent another subject of particular relevance in the present invention, as does hens and chicken, but also pigs, and in a particular embodiment also fish. In a preferred embodiment the subject is a fish, a fish larvae, a shell fish, or a shell fish larvae. Other preferred embodiments include subjects selected from the group of cultured fish, cultured shellfish or cultured larvae, such as fish, shell fish and larvae from fish farms.

Infant Formulation

An infant formulation is often a milk substitute specially manufactured to satisfy, by itself, the nutritional requirements of infant subjects during the first time of life up to the introduction of appropriate complementary feeding. In humans, term infant means a subject not more than 12 months of age. Infant formulations may be a product based on milk of cows or other animals or a mixture thereof and/or other ingredients which have been proven to be suitable for infant feeding. The nutritional safety and adequacy of an infant formulation should be scientifically demonstrated to support growth and development of infants. The term "infant formulation" as used herein refers to a nutritional composition designed for subjects of 12 months of age, or younger, which contains sufficient protein, carbohydrate, fat, vitamins, minerals, and electrolytes to serve as the sole source of the nutrition for these subjects, when provided in a sufficient quantity.

In one aspect the present invention relates to an infant formulation comprising a germ free composition comprising colostrum. In another aspect the present invention relates to an infant formulation comprising a germ free composition comprising colostrum enriched with synthetically multimerised immunoglobulins. Another aspect relates to the use of the compositions of the present invention as an infant formulation for a subject, wherein the subject in one embodiment is a calf. In a preferred embodiment the subject is a human not more than 12 months of age.

The milk replacer, food supplement, growth promoter and infant formulation of the present invention as described herein, may be administered orally, enterically or rectally as a ready-to-feed liquid, a concentrate that is diluted prior to consumption or a powder that is reconstituted or dissolved prior to consumption. In addition to these, the form of administration may include a tablet and any liquid resulting from the reconstitution or dissolution of such tablets. In a preferred embodiment the compositions of the present invention is administered orally.

Formulations

Whilst it is possible for the compositions or salts of the present invention to be administered as the raw chemical, it is preferred to present them in the form of a pharmaceutical formulation. Accordingly, the present invention further provides a pharmaceutical formulation, for medicinal application, which comprises a composition of the present invention or a pharmaceutically acceptable salt thereof, as herein defined, and a pharmaceutically acceptable carrier therefore.

The compositions of the present invention may be formulated in a wide variety of oral administration dosage forms. The pharmaceutical compositions and dosage forms may comprise the compositions of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, lubricants, suspending agents, binders, preservatives, wetting agents, tablet disintegrating agents, or an encapsulating material.

Preferably, the composition will be about 0.5% to 75% by weight of a composition or compositions of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. The powders and tablets preferably contain from one to about seventy percent of the active composition. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active composition with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, suspensing and emulsifying agents, and the like.

Other forms suitable for oral administration include liquid form preparations including emulsions, syrups, elixirs, aqueous solutions, aqueous suspensions, toothpaste, gel dentifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by suspending or mixing the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include suspensions and emulsions, and may contain, in addition to the active component, colorants, flavors, stabilizers, buffers, artificial and natural sweeteners, dispersants, thickeners, and the like.

The compositions of the invention can also be delivered topically. Regions for topical administration include the skin surface and also mucous membrane tissues of the vagina, rectum, nose, mouth, and throat. Compositions for topical administration via the skin and mucous membranes should not give rise to signs of irritation, such as swelling or redness.

In a particular embodiment topical delivery og the compositions of the present invention is for treatment of skin conditions such as wounds, The topical composition may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

The compositions of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatine and glycerin or sucrose and acacia; and mouthwashes comprising the active ingredient in a suitable liquid carrier.

Creams, ointments, gels, balms, or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention include those suitable for application to the skin or eye. In a preferred embodiment the lotions of the present invention is for topical application to the skin. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil, jojoba, arachis oil, simmondsia chinensis oil, olea europaea fruit oil, aracis hypogae oil, prunus amygdalus dulcis oil.

In one embodiment of the present invention the composition is in the form of a lip balm, gel, mask, ointment, cream, lotion and/or shampoo.

An Immunoglobulin Product Devoid of Pathogens

Accordingly the invention provides a product for administration to a newborn mammal characterized by
  a. a concentration of immunoglobulin corresponding to at least 10%, such as at least 15%, such as at least 20%, such as at least 25%, such as at least 30%, such as at least 35%, such as at least 40%, such as at least 50% on a dry matter basis.
  b. having been exposed to a treatment making it free of one or more or all pathogenic microorganisms, which treatment substantially avoids negative impact on the biological activity of the immunoglobulins and/or the feeding characteristics such as the texture and/or viscosity of the product.

In still a preferred embodiment one or more or all of the chemical substance(s) have been removed from the product after inactivating the pathogenic microorganism(s).

Preferably the product comprises natural colostrum, natural milk, milk concentrate, whey or whey concentrate.

Further, in another aspect of the invention, the new born mammal, such as the new born calf, is separated from the dam before it reaches the udder and starts suck colostrum from the dam followed by feeding the new born mammal with a colostrum, colostrum replacer, colostrum supplement or a combination of these treated to inactivate or remove pathogenic microorganisms according to the invention.

An Antimicrobial Composition for Administration to a Newborn Farm Production Animal In yet an aspect of the present invention a composition comprising a conjugate comprising one or more chemically and covalently polymerised monomeric substances having an anti-microbial activity, wherein the conjugate comprises at least 4 active sites and the active sites contributes to an antimicrobial activity, is provided.

In a further aspect of the present invention a method is provided for producing a covalent polymerised conjugate of at least two substances having antimicrobial activity, said method comprises the steps of:
  (i) selecting a substance having antimicrobial activity,
  (ii) subjecting the substance from step (i) to chemical treatment, and
  (iii) allowing the chemically treated substance from step (ii) to polymerise to provide covalent polymerised conjugate having antimicrobial activity.

In yet aspect of the present invention a pharmaceutical composition, a feed supplement and a food product comprising the conjugate described herein is provided.

An Immunoglobulin Product Devoid of Pathogens

The present invention provides a product for administration to a newborn mammal characterized by
  a. a concentration of immunoglobulin corresponding to at least 10%, such as at least 15%, such as at least 20%, such as at least 25%, such as at least 30%, such as at least 35%, such as at least 40%, such as at least 50% on a dry matter basis.
  b. having been exposed to a treatment to inactivate one or more or all pathogenic microorganisms, which treatment substantially avoids negative impact on the biological activity of the immunoglobulins and/or the feeding characteristics such as the texture and/or viscosity of the product.

In a preferred embodiment the treatment comprises a step exposing the immunoglobulin product to one or more chemical substances to inactivate one or more or all pathogenic microorganisms.

The chemical substance(s) are selected from the group of disinfectant dyes such as artificial organic dyes, generally known as "vital dyes," including methylene blue and related thionine dyes (electronegative), acridine orange, acridine yellow and related acriflavine (acridine) dyes (electropositive), proflavine hemisulphate, quinacrine and its derivatives, brilliant green, gentian violet, crystal violet and related triphenyl methane dyes (electropositive), and bis naphthalene dyes such as trypan blue and trypan red and combinations hereof.

Preferred Items

Preferred items relating to the present invention are disclosed herein below:

1 A product for administration to a newborn mammal characterized by
  a. a concentration of immunoglobulin corresponding to at least 10%, such as at least 15%, such as at least 20%, such as at least 25%, such as at least 30%, such as at least 35%, such as at least 40%, such as at least 50% on a dry matter basis.
  b. having been exposed to a treatment to inactivate one or more or all pathogenic microorganisms, which treatment substantially avoids negative impact on the biological activity of the immunoglobulins and/or the feeding characteristics such as the texture and/or viscosity of the product;
wherein the treatment comprises a step exposing the immunoglobulin product to one or more chemical substances to inactivate one or more or all pathogenic microorganisms.

2 A product according to item 1 wherein one or more or all of the chemical substance(s) have been removed from the product after inactivating the pathogenic microorganism(s).

3 A product according to items 1 and 2 wherein the chemical substance(s) are selected from the group of disinfectant dyes such as artificial organic dyes, generally known as "vital dyes," including methylene blue and related thionine dyes (electronegative), acridine orange, acridine yellow and related acriflavine (acridine) dyes (electropositive), quinacrine and its derivatives, brilliant green, gentian violet, crystal violet and related triphenyl methane dyes (electropositive), and bis naphthalene dyes such as trypan blue and trypan red.

4 A product according to item 1-3 wherein the chemical substance(s) further comprise a reducing agent, such as ascorbic acid.

5 A product according to item 1-4 wherein the chemical substance(s) further comprise a cell lysing agent such as a detergent.

6 A product according to item 2-5 wherein one or more or all the chemical substance(s) are removed by adsorption.

7 A product according to item 1-6 wherein the pathogenic microorganism is *mycobacterium paratuberculosis*

8 A product according to item 1-7 wherein the immunoglobulin is a purified native immunoglobulin.

9 A product according to item 1-7 wherein the immunoglobulin is a purified native immunoglobulin being treated by sterile filtration such as by microfiltration or by ultrafiltration.

10 A product according to item 1-7 wherein the immunoglobulin is a purified native immunoglobulin being treated by radiation such as UV-radiation or gammaradiation.

11 A product according to item 1-7 wherein the immunoglobulin is a purified native immunoglobulin being treated by pasteurisation.

12 A product according to item 8-11 wherein the immunoglobulin is isolated from milk, colostrum, whey, blood, serum, plasma or any derivatives or fractions of such raw materials.

13 A product according to item 1-12 wherein the immunoglobulin is originating from farm production animals such as cows, goats, sheep and pigs.

14 A product according to item 1-7 wherein the product comprises natural colostrum, milk, milk concentrate, whey or whey concentrate.

15 A method for the prevention of pathogenic microbial infection of a newborn mammal through ingestion of natural infected colostrum, natural infected milk and infectious colostrum and milk substitutes and replacers comprising the steps of:
  a. ensuring that the newborn mammal does not ingest any colostrum from the dam preferably by separating the dam and the newborn mammal before the mammal starts sucking.
  b. administer a liquid comprising soluble immunoglobulins having been exposed to a treatment to inactivate one or more or all pathogenic microorganisms and having a high concentration of native immunoglobulins to reach a total immunoglobulin administration within the first 36 hours such as within the first 24 hours after birth of at least 20 gram IgG, such as at least 30 gram IgG, such as at least 40 gram IgG, such as at least 50 gram IgG, such as at least 75 gram IgG, such as at least 100 gram IgG, such as at least 125 gram IgG, such as at least 150 gram IgG, such as at least 200 gram IgG, such as at least 250 gram IgG;
wherein the treatment comprises a step exposing the immunoglobulin product to one or more chemical substances to inactivate one or more or all pathogenic microorganisms.

16 A method according to item 15 wherein one or more or all of the chemical substance(s) have been removed from the liquid after inactivating one or more or all the pathogenic microorganisms and prior to administration to the newborn mammal.

17 A method according to items 15 and 16 wherein the chemical substance(s) are selected from the group of disinfectant dyes such as artificial organic dyes, generally known as "vital dyes," including methylene blue and related thionine dyes (electronegative), acridine orange, acridine yellow and related acriflavine (acridine) dyes (electropositive), quinacrine and its derivatives, brilliant green, gentian violet, crystal violet and related triphenyl methane dyes (electropositive), and bis naphthalene dyes such as trypan blue and trypan red.

18 A method according to item 17 wherein the chemical substance(s) further comprise a reducing agent, such as ascorbic acid.

19 A method according to item 15-18 wherein the chemical substance(s) further comprise a cell lysing agent such as a detergent.

20 A method according to item 15-19 wherein one or more or all of the chemical substance(s) are removed by adsorption.

21 A method according to item 14-19 wherein the pathogenic microorganism is *mycobacterium paratuberculosis*.

22 A method according to item 14 wherein the immunoglobulin is a purified native immunoglobulin.

23 A method according to item 15 wherein the immunoglobulin is a purified native immunoglobulin being treated by sterile filtration including microfiltration and ultrafiltration.

24 A method according to item 15 wherein the immunoglobulin is a purified native immunoglobulin being treated by irradiation such as UV-irradiation or electromagnetic irradiation.

25 A method according to item 15 wherein the immunoglobulin is a purified native immunoglobulin being treated by pasteurisation.

26 A method according to item 22-25 wherein the immunoglobulin is isolated from milk, colostrum, whey, blood, serum, plasma or any derivatives or fractions of such raw materials.

27 A method according to item 15-26 wherein the immunoglobulin is originating from farm production animals such as cows, goats, sheep and pigs.

28 A method according to item 1-7 wherein the liquid comprising soluble immunoglobulins is a natural colostrum, milk, milk concentrate, whey or whey concentrate.

29 A composition for administration to a newborn farm production animal comprising a conjugate comprising one or more chemically and covalently polymerised monomeric substances originating from farm production animals and having an antimicrobial activity, wherein the conjugate comprises at least 4 active sites and the active sites contributes to an antimicrobial activity.

30 A composition according to item 29 wherein the polymeric compound carry at least 6, such as at least 8, such as at least 10, such as at least 12, such as at least 20, such as at least 30, such as at least 50, such as at least 100 of said active sites.

31 A composition according to items 29 or 30 wherein the two or more monomeric substances comprises two or more proteins or two or more peptides having antimicrobial activity.

32 A composition according to item 29-30 wherein the two or more monomeric substances, such as 3 or more monomeric substances, e.g. 4 or more monomeric substances, such as 5 or more monomeric substances, e.g. 10 or more monomeric substances, such as 15 or more monomeric substances, e.g. 20 or more monomeric substances, such as 50 or more monomeric substances, e.g. 100 or more monomeric substances, comprise one or more immunoglobulin classes selected from the group of IgG, IgA, IgM, IgE, IgD, IgY, such as 2 or more immunoglobulin classes, e.g. 3 or more immunoglobulin classes, such as 4 or more immunoglobulin classes, e.g. 5 or 6 immunoglobulin classes.

33 A composition according to item 32 wherein the immunoglobulin is isolated from bovine milk or bovine blood.

34 A composition according to item 32 wherein the immunoglobulin is isolated from porcine blood.

35 A composition according to item 32 wherein the immunoglobulin is isolated from avian eggs or avian blood.

36 A composition according to item 32 wherein the immunoglobulin is isolated from milk, eggs or blood derived from animals selected from the group of: horses, goats, sheep, pigs, camels, hens, ducks, geese, cows.

37 A composition according to item 32 wherein the immunoglobulin is isolated from transgenic animals, transgenic plants or other genetically modified organism.

38 A composition according to item 29-36 wherein the immunoglobulin is isolated from vaccinated animals.

39 A composition according to item 32-38 wherein the immunoglobulin is an immunoglobulin fragment.

40 A composition according to item 32-39 wherein the two or more monomeric substances further comprise a non-immunoglobulin substance having anti-microbial activity.

41 A composition according to item 40 wherein the non-immunoglobulin substance is selected from the group of lactoferrin, transferrin, ovotransferrin, lysozyme, antimicrobial peptides such as nicin, cathelicidins, defensisn, dermeidin, magainin 2, protegrin, protegrin-1, melittin, 11-37, dermaseptin 01, cecropin, caerin, ovispirin, and alamethicin.

42 A composition according to items 29-31 wherein the one or more monomeric substances comprise lactoferrin.

43 A composition according to item 29-31 wherein the one or more monomeric substances comprise transferrin.

44 A composition according to item 29-31 wherein the one or more monomeric substances comprise ovotransferrin.

45 A composition according to item 29-31 wherein the one or more monomeric substances comprise lysozyme.

46 A composition according to item 29-45 wherein the two or more monomeric substances, such as 3 or more monomeric substances, e.g. 4 or more monomeric substances, such as 5 or more monomeric substances, e.g. 10 or more monomeric substances, such as 15 or more monomeric substances, e.g. 20 or more monomeric substances, such as 50 or more monomeric substances, e.g. 100 or more monomeric substances, comprise one or more substances without anti microbial activity, such as 2 or more substances without anti-microbial activity, e.g. 3 or more substances without anti-microbial activity, such as 5 or more substances without anti-microbial activity, e.g. 10 or more substances without anti-microbial activity, such as 15 or more substances without anti-microbial activity, e.g. 20 or more substances without anti-microbial activity, such as 50 or more substances without anti-microbial activity, e.g. 100 or more substances without anti-microbial activity.

47 A composition according to item 46 wherein the one or more substances without antimicrobial activity is chosen from the group of proteins, polysaccharides, other natural or synthetic polymers.

48 A composition according to item 46 wherein the one or more substances without anti-microbial activity is chosen from the group of: albumin, beta-lactoglobulin, alpha-lactalbumin, casein, chitosan, dextran, cellulose and derivatives of these.

49 A composition according to item 29-48 wherein the one or more monomeric substances are polymerised by way of reaction with a carbohydrate part carried by the monomeric substance.

50 A composition according to item 49 wherein the carbohydrate part is oxidised with periodate to create aldehyde groups capable of reacting with amino-groups carried by other molecules.

51 A composition according to item 50 wherein reaction with amino-groups carried by other molecules is performed in the presence of lyotropic salt or other water structuring substances such as polyethylene glycol.

52 A composition according to item 51 wherein the concentration of lyotropic salt or other water structuring substance is at least 1% w/w, such as at least 2% w/w such as at least 3% w/w such as at least 4% w/w, such as at least 5% w/w, such as at least 7% w/w, such as at least 10% w/w.

53 A method for providing a covalent polymerised conjugate of at least two substances having antimicrobial activity, said method comprises the steps of: (i) selecting a substance having antimicrobial activity, (ii) subjecting the substance from step (i) to chemical treatment, and (iii) allowing the chemically treated substance from step (ii) to polymerise to provide covalent polymerised conjugate having antimicrobial activity.

54 A method according to item 53 wherein the substance is a protein or a peptide.

55 A method according to any one of items 53 or 54 wherein substance comprises at least one carbohydrate moiety.

56 A method according to any one of items 53-55 wherein the chemical treatment is an oxidation treatment.

57 A method according to item 56, wherein the oxidation treatment is performed in the presence of periodate.

58 A method according to any one of items 53-57, wherein the polymerisation in step (iii) is performed in the presence of a salt, such as a lyotrophic salt, or other water structuring substances, such as polyethylene glycol.

59 A pharmaceutical composition comprising the conjugate according to items 29-52 and a pharmaceutical acceptable carrier.

60 A feed supplement for a mammal comprising the conjugate according to items 29-52.

61 The feed supplement according to item 59 wherein the mammal is selected from the group consisting of horse, goat, sheep, pig, camel, hens, duck, geese, cow and humans.

62 A food product comprising the conjugate according to items 29-52.

63 A method for passive immunisation of a mammal to prevent or treat microbial infection at mammal skin and/or mucosal surfaces, said method comprises the step of administering a pharmaceutical effective amount of the conjugate according to items 29-52.

64 A method for the treatment or prevention of diarrhoea (travellers disease), said method comprises the step of administrating a pharmaceutical effective amount of the conjugate according to items 29-52.

65 A method for the prophylaxis treatment and treatment of microbial inflammation in patients suffering from diseases suppressing the immune system, said method comprises the step of administrating a pharmaceutical effective amount of the conjugate according to items 29-52.

66 Use of the conjugate according to any one of items 29-52 for the preparation of a medicament for the prevention and/or treatment of microbial infection.

67 Use of the conjugate according to any one of items 29-52 as a growth enhancer.

68 Use of the conjugate according to any one of items 29-52 for the preparation of a medicament for the prevention and/or treatment of diarrhoea (travellers disease).

69 Use of the conjugate according to any one of items 29-52 as milk replacer for a new born mammal.

70 The use according to item 69, wherein the mammal is selected from the group consisting of horse, goat, sheep, pig, camel, hens, duck, geese, cow or human.

71 Use of the conjugate according to items 29-52 for the preparation of a medicament for the prophylaxis treatment and treatment of microbial inflammation in patients suffering from diseases suppressing the immune system.

72 The use according to item 71 wherein the patients suffering from diseases suppressing the immune system is patients suffering from AIDS and cancer. 73 Use of the conjugate according to items 29-52 for healing wounds.

EXAMPLES

Example 1

Isolation of Immunoglobulin G from Sweet Whey Utilising Expanded Bed Adsorption

Isolation Procedure

Non-pasteurised sweet whey was obtained from cheese production at a local Danish dairy. 3150 L sweet whey was adjusted to 5.0 with hydrochloric acid before being loaded onto an expanded bed adsorption column (Rhobust Flex 45 cm i.d., UpFront Chromatography, Denmark) containing 105 L adsorbent (tungsten carbide—agarose conglomerate beads comprising an anionic mixed mode as IgG binding ligand, bead density=3.1 kg per L, mean particle size=190 micron, UpFront Chromatography A/S, Denmark). The settled bed height of the adsorbent was 64 cm.

The sweet whey, which had a conductivity of 6.5 mS/cm was loaded onto the column using a linear flow rate of 9 cm/min.

All procedures were performed at ambient temperature.

Following load of the sweet whey to the expanded bed column, the adsorbent was washed by loading 750 L of a washing buffer (10 mM sodium citrate, 0.35 mg/ml caprylic acid, 40 mM NaCl, pH 5.5, 6.5 mS/cm) at the same linear flow rate (9 cm/min). This washing procedure ensured that most unbound and loosely bound substances from the sweet whey were removed from the column and adsorbent prior to elution of the reversibly bound immunoglobulin fraction.

Following washing the bound immunoglobulins were released and eluted from the column by applying 500 L of an elution buffer (20 mM $Na_2CO_3$, pH 10.0, conductivity=3.7 mS/cm). The peak of released protein was detected using a UV-monitor indicating the absorbance of light with a wavelength of 280 nm. Collection of the eluate was performed to obtain all the eluted protein in one fraction according to the UV-monitor signal. The immunoglobulin eluate was collected in a volume of 350 L and the pH herein was adjusted to pH 7 with 1 M hydrochloric acid. The IgG eluate was then concentrated by ultrafiltration on a hollow fiber ultrafilter having a nominal molecular weight cut-off of 10.000 Dalton (Pall Corporation, USA). Ultrafiltration was performed over 6 hours to a final retentate volume of 14.5 L and the concentrate was labeled "Concentrated IgG Eluate" The concentrate was frozen in aliquots of 500 ml at −18 degrees Celsius.

The column was then thoroughly rinsed and regenerated by loading 350 L of a regeneration buffer (0.2 M NaOH) followed by 200 L of an equilibration buffer (10 mM sodium citrate pH 5.0, 2.6 mS/cm). The column was then ready for the next cycle with a new batch of sweet whey.

Analysis

The concentration of IgG in the immunoglobulin eluate was determined by Single Radial Immuno-diffusion (RID). Rabbit anti-bovine immunoglobulins from Dako Cytomation, Denmark (Cat. no.: Z247) was used. A highly purified bovine IgG of known concentration was used as a standard in the assay.

Dry matter determination was performed to determine the total dry matter contents of the IgG eluate. A sample of the eluate was first dialysed against demineralised water followed by drying of the sample to constant weight at 110 degrees Celsius.

The sweet whey raw material and the IgG eluate were analysed for the presence of bovine anti-rotavirus antibodies. The assay was based on a ELISA procedure using assay kits from Cypress Diagnostics, Belgium (VB081).

The IgG eluate was further tested with sodium dodecyl polyacrylamide gelelectrophoresis (SDS-PAGE, Progel, Tris-glycine, 4-20%, 1.0 mm; Anamed, Darmstadt, Germany) to evaluate the content and nature of the proteins present in the eluate. The SDS-PAGE gels were stained with Coomassie Blue and the relative intensity of the stained protein bands was determined with scanning densitometry.

The composition of the Concentrated IgG Eluate was further characterised by gel permeation chromatography using an Akta purifier P900 and a Superdex 200 column, 10 mm i.d. 30 cm bed height, flow rate 1 ml/min. (GE Healthcare, Uppsala, Sweden). The mobile buffer used was 50 mM potassium phosphate plus 0.1 M sodium chloride, pH 7.0.

Results

The Concentrated IgG Eluate was a clear, brown liquid (the colour being caused mainly by the content of lactoperoxidase and lactoferrin co-purified with the IgG). No protein precipitation was observed.

Single radial immuno-diffusion indicated that the IgG eluate had an IgG concentration of 3.15 g/L corresponding to a total IgG content of 3.15 g/L×350 L=1103 g IgG or 1.103 kg IgG.

Dry matter determination of the eluate indicated the presence of a total of 1.43 kg protein in the IgG elution fraction.

ELISA testing for the presence of anti-rotavirus antibodies in the sweet whey raw material indicated a considerable amount of active antibody activity (1000 fold dilution needed to reach 50% inhibition in the assay). Assaying the IgG eluate indicated that more than 80% of the total anti-rotavirus antibodies were isolated in the IgG eluate. This result further indicates that the isolation procedure applied is gentle and conserves the biological activity of the fragile immunoglobulin molecules to a high degree.

SDS-PAGE of the eluted IgG confirmed that IgG was the major protein present in the eluate, minor bands representing the presence of other proteins indicated that the majority of other proteins was constituted by lactoferrin, lactoperoxidase and albumin. Scanning densitometry indicated that the IgG band constituted approx. 80% of the total protein.

Gel permeation chromatography (FIG. 1) indicated a major protein peak at a retention time of approx. 11.8 minutes. This is in correspondence with the molecular weight of IgG being approx. 150.000 Dalton and the fact that IgG constitutes the major part of the protein in the eluate. The UV trace of the gel permeation chromatography further indicates the presence of a small amount of higher molecular weight proteins/compounds (eluting from about the 7.0 min to the 10.0 min. retention time mark).

Example 2

Multimerization of IgG Isolated from Sweet Whey

The purpose of the following example was to demonstrate the transformation of the mainly monomeric IgG molecules isolated in example 1 into multimeric, covalently assembled, agglomerates comprising several IgG molecules. The Concentrated IgG Eluate described in Example 1 was used as raw material.

Multimerisation Procedure

All procedures were performed at ambient temperature.

Three samples of the Concentrated IgG Eluate were adjusted to pH 5.5 using 1M acetic acid.

Sodium periodate (cat. No.: 30323, Sigma-Aldrich, USA) was added under gentle mixing to the concentrate to reach a concentration of A) 10 mM periodate B) 20 mM periodate and C) 40 mM periodate in three separate samples. The solution was then stored without mixing in the dark for 1 hour followed by adjusting to pH 9.5 using 1 M sodium hydroxide and then left without mixing at room temperature for 24 hours. Hereafter pH was adjusted to pH 7.0 with 1 M hydrochloric acid and the solutions A), B) and C) were analysed as described below.

Analysis

The effect of the multimerization procedure was evaluated by gel permeation chromatography and RID in comparison to the starting material for each of the samples A), B) and C) as described in example 1.

Results

Figure 2:
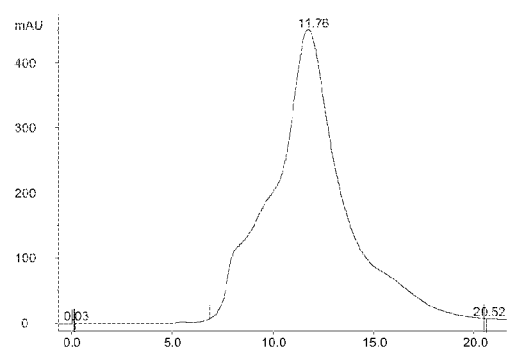
FIG. 2 illustrates the UV trace (280 nm) of gel permeation chromatography analysis of the starting material and samples A-C according to example 2.
Figure 2:
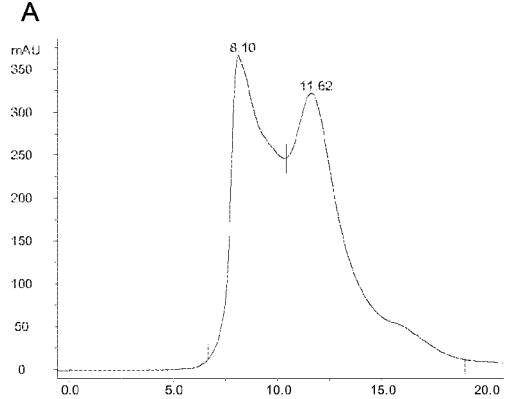
Figure 2:
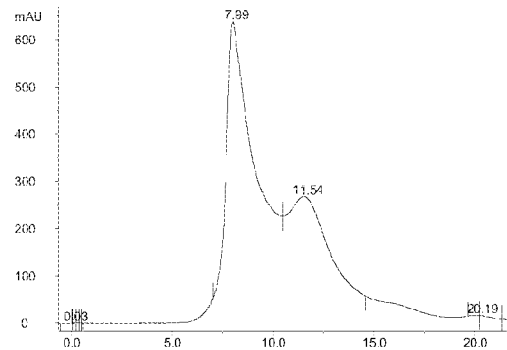
Figure 2:
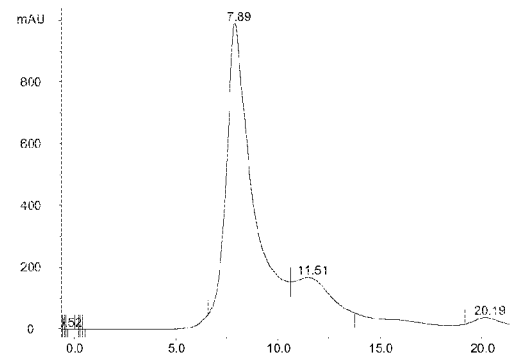

All samples remained clear without any protein precipitation occurring. UV-traces of the gel permeation chromatography of the samples A), B) and C), (FIG. 2), illustrate that the molecular weight distribution changes in a dose dependent manner relative to the amount of periodate added to the IgG solution. In comparison to the starting material, sample A (10 mM periodate) has approximately 50% of the IgG polymerised to form aggregates having a retention time below the 10 minutes mark (corresponding to molecular weights of the aggregates varying from about 300,000 Dalton to about 1,000,000 Dalton and above. In sample B (20 mM periodate) approximately 65% of the IgG is polymerised to form aggregates having a retention time below the 10 minutes mark. In sample C (40 mM periodate) approximately 80% of the IgG is polymerised to form aggregates having a retention time below the 10 minutes mark.

For all three samples analysis by RID confirmed that the multimeric molecules were still immuno-reactive and formed well-defined precipitation rings.

Example 3

Multimerization of IgG Directly in Colostrum Whey

The purpose of the following example was to transform the mainly monomeric immunoglobulin molecules naturally present in colostrum into multimeric, covalently assembled, agglomerates comprising several immunoglobulin molecules. Bovine colostrum whey prepared by casein precipitation of crude colostrum was used as raw material.

Multimerisation Procedure

All procedures were performed at ambient temperature.

Bovine colostrum was collected from a local Danish farm using only the first 2 days of milking after parturition. Pooled colostrum was adjusted to pH 4.5 with 1 M hydrochloric acid and centrifuged. The clear supernatant was decanted and utilised for the multimerisation procedure.

Three samples of the colostrum whey were adjusted to pH 5.5 using 1M acetic acid.

Sodium periodate (cat. No.: 30323, Sigma-Aldrich, USA) was added under gentle mixing to the colostrum samples to reach a concentration of A) 0 mM periodate (control) B) 40 mM periodate and C) 100 mM periodate in three separate samples. The solution was then stored without mixing in the dark for 1 hour followed by adjusting to pH 9.5 using 1 M sodium hydroxide and then left without mixing at room temperature for 24 hours. Hereafter pH was adjusted to pH 7.0 with 1 M hydrochloric acid and the solutions A), B) and C) were analysed as described below.

Analysis

The effect of the multimerization procedure was evaluated by gel permeation chromatography and RID for each of the samples A), B) and C) as described in example 1.

Results

Figure 3:
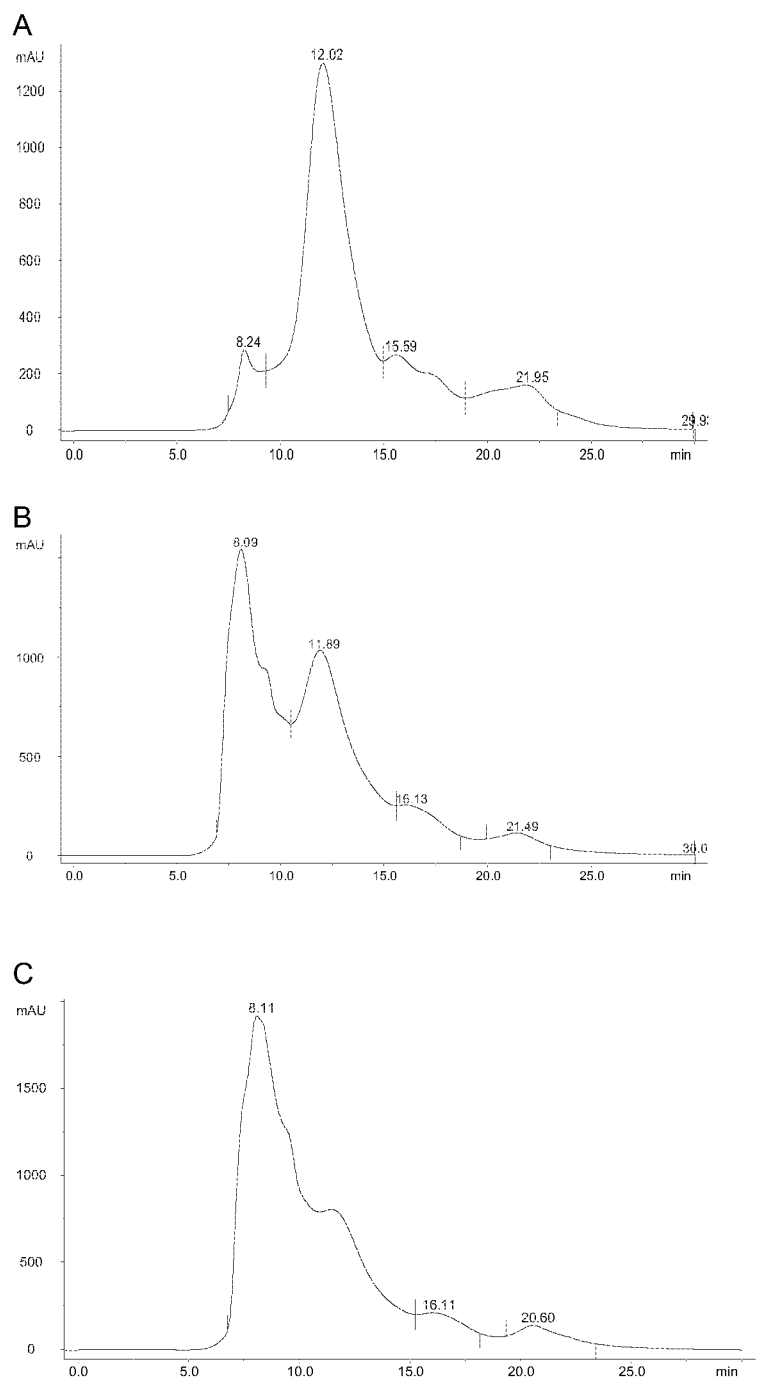
FIG. 3 illustrates the UV trace (280 nm) of gel permeation chromatography analysis of samples A-C according to example 3.

UV-traces of the gel permeation chromatography of the samples A), B) and C), (FIG. 3), illustrate that the molecular weight distribution changes in a dose dependent manner relative to the amount of periodate added to the IgG solution. In sample A (0 mM periodate, control) only a very small amount of protein is of high molecular weight having a retention time below the 10 minutes mark. In sample B (40 mM periodate) approximately 60% of the protein is polymerised to form aggregates having a retention time below the 10 minutes mark. In sample C (100 mM periodate) approximately 80% of the protein is polymerised to form aggregates having a retention time below the 10 minutes mark.

RID confirmed that the multimeric molecules were still immuno-reactive and formed well-defined precipitation rings.

Example 4

Multimerization of IgG Directly in Porcine Plasma

The purpose of the following example was to transform the mainly monomeric immunoglobulin G molecules naturally present in porcine plasma into multimeric, covalently assembled, agglomerates comprising several immunoglobulin molecules.

Multimerisation Procedure

All procedures were performed at ambient temperature.

Porcine plasma was sourced from local Danish abattoirs.

The plasma was adjusted to pH 5.5 using 1M acetic acid.

Sodium periodate (cat. No.: 30323, Sigma-Aldrich, USA) was added under gentle mixing to the plasma to reach a concentration of A) 0 mM periodate, control sample and B) 60 mM periodate. The solutions were then stored without mixing in the dark for 1 hour followed by adjusting to pH 9.5 using 1 M sodium hydroxide and then left without mixing at room temperature for 24 hours. Hereafter pH was adjusted to pH 7.0 with 1 M hydrochloric acid.

Analysis

The effect of the multimerization procedure was evaluated by gel permeation chromatography as described in example 1.

Results

Figure 4:
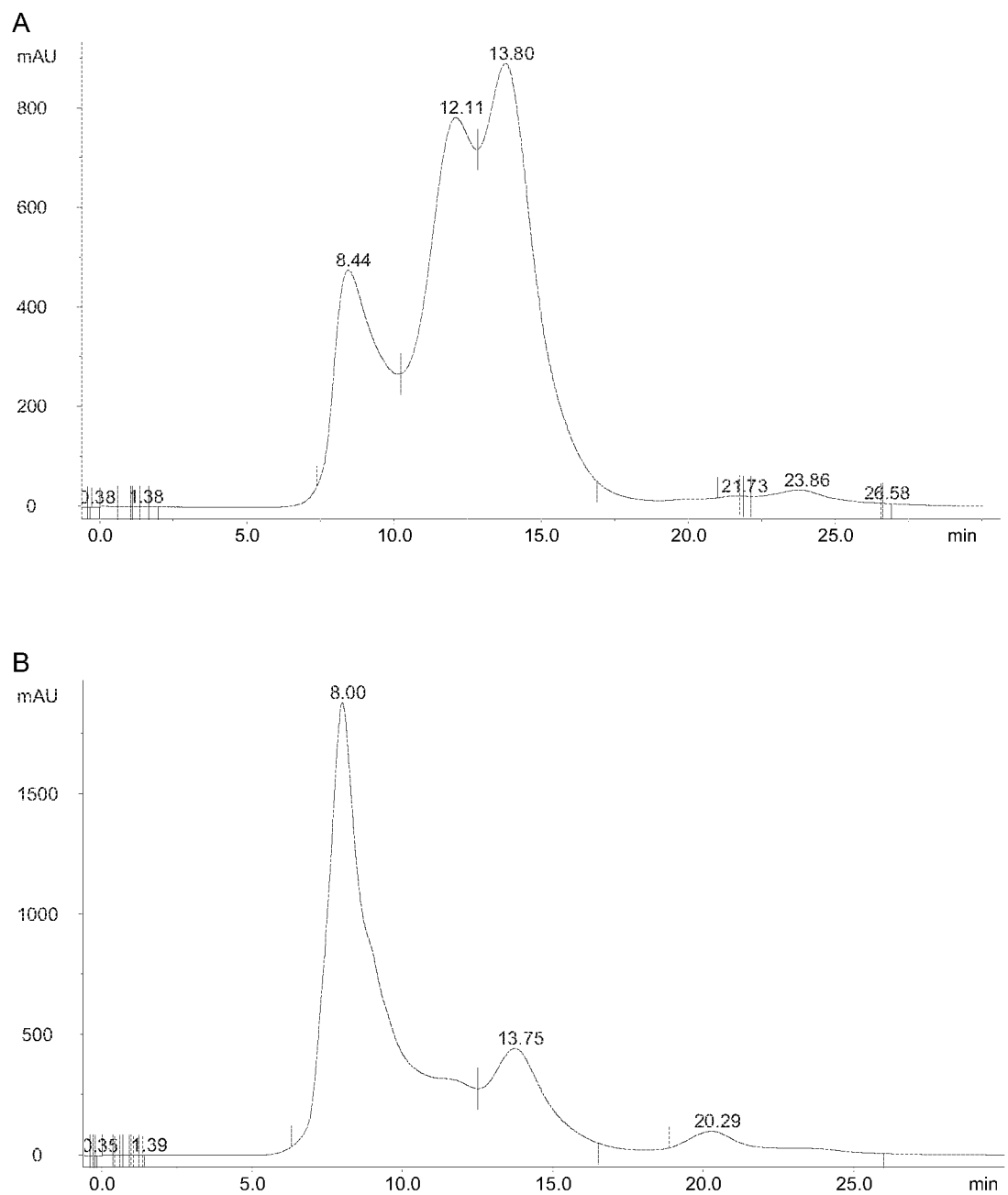
FIG. 4 illustrates the UV trace (280 nm) of gel permeation chromatography analysis of samples A-B according to example 4.

UV-traces of the gel permeation chromatography of the samples A) and B), (FIG. 4), illustrate that the molecular weight distribution changes extensively when periodate has been added to the porcine plasma. In sample A (control, 0 mM periodate) approximately 20% of the protein is having a retention time below the 10 minutes mark. In sample B (60 mM periodate) approximately 70% of the protein is polymerised to form aggregates having a retention time below the 10 minutes mark.

From this it can further be concluded that other proteins than IgG (e.g. albumin and transferrin) also are forming part of the high molecular weight aggregate.

Example 5

Adsorption of Immunoglobulins from Colostrum Whey, Bioburden Reduction and Recombination The purpose of the following example was to demonstrate the principle of removing the bioactive immunoglobulins from colostral whey by adsorption followed by sterilisation of the separated components by different sterilising/disinfection treatments followed by recombination of the components to obtain a near sterile and highly bio-active colostrum product.

Procedure

Bovine colostrum was collected from a local Danish farm using only the first 2 days of milking after parturition. Pooled colostrum was diluted one to one with demineralised water and adjusted to pH 4.5 with 1 M hydrochloric acid and centrifuged. The clear supernatant was decanted and utilised for the procedure.

50 L of the diluted colostral whey was adjusted to pH 5.2 with 1 M sodium hydroxide and applied to the same adsorption column as described in example 1. Following the same general procedure as in example 1 there was obtained an immunoglobulin eluate (385 L), which was concentrated to 100 g/L dry matter by ultrafiltration followed by sterilisation by micro-filtration on a 0.2 micron membrane filter into autoclaved glass containers (in total 1.5 kg protein on a dry matter basis).

The non-bound colostral whey fraction (run-through) was collected prior to elution of bound immunoglobulins and hereafter treated by pasteurisation at 138 degrees Celsius for 1 second (UHT pasteurisation). The sterilised colostral whey fraction was then recombined with the sterilised immunoglobulin eluate under aseptic conditions and packaged into autoclaved glass containers.

Analysis

RID (see example 1) was used to determine the adsorption efficiency and concentration of IgG in the immunoglobulin eluate and an ELISA test (see example 1) was performed to test for the quantitative presence of bovine anti-rotavirus antibodies before and after the procedure.

Results

The immunoglobulin concentration in the eluate was determined by RID to be 3.3 g/L (in total 1155 gram IgG). ELISA testing confirmed that practically all the bovine anti-rotavirus antibodies present in the initial colostral whey fraction was still present and immunologically reactive in the sterilised and re-combined colostral whey.

Example 6

Adsorption of Immunoglobulins from Colostrum Whey, Bioburden Reduction, Multimerisation and Recombination The purpose of the following example was to demonstrate the principle of removing the bioactive immunoglobulins from colostral whey by adsorption followed by sterilisation of the separated components by different sterilising/disinfection treatments followed by multimerisation of the isolated immunoglobulins prior to recombination of the components to obtain a near sterile and highly bio-active multimeric colostrum product.

Procedure

The procedure described in example 4 was followed to produce the sterilised colostral whey components. The concentrated IgG eluate was treated as described in example 2 using 40 mM sodium periodate and then recombined with the UHT treated colostral whey fraction.

Results

Analysis showed that the recombined sterilised colostral whey fraction comprised a significant amount of polymerised IgG molecules as demonstrated in example 2.

Example 7

Inactivation of Microorganisms in Colostrum using Double Dye Method

Bovine colostrum was collected from a local Danish farm using only the first 2 days of milking after parturition.

Dye Treatment

Colostrum was treated with various concentrations of a solution containing methylene blue and crystal violet (double dye solution) and ascorbic acid.

The dye treatments were carried out at pH 6.5 at ambient temperature.

10 ml Double Dye stock solution containing 1 w/v % crystal violet and methylene blue, respectively:

0.1 g crystal violet (Sigma Aldrich) diluted in 10 ml 1% methylene blue (Bie & Berntsen, Copenhagen, Denmark)

2% Ascorbic acid stock solution:

0.2 g ascorbic acid to 10 ml demineralised water.

Aliquots of 25 ml colostrum was added various amounts of the Double Dye sock solution to obtain a final concentration of double dye of 0.001%; 0.01%; 0.05% and 0.1% w/v % respectively. All solutions were added ascorbic acid to reach the same final concentration as the respective double dye concentration.

After standing in a closed container for 2 hours at room temperature, plate count was carried out on the dye treatments and the untreated colostrum.

Plate count, CFU:

The impact of the Double Dye treatment was evaluated by plate count.

A 10-fold serial dilution (in sterile 1×PBS buffer) was carried out on the treated control and each dye treatment. 100 µl from each dilution: undiluted, $10^{-1}$ and $10^{-2}$, was inoculated on Plate Count Agar "Merkoplate" from Merck.

Colony counts were obtained after incubation of the plates for 24 h at 37° C.

Results

The disinfection ability of the double dye method was clearly demonstrated but required an unexpectedly high dose to become effective. Only at the highest double dye concentrations (0.05% and 0.1%) an efficient bacterial kill was observed.

Example 8

Dye Treatment for Removing *Mycobacterium avium* ssp. *paratuberculosis*

To monitor the efficiency of dye treatment for removing *Mycobacterium avium* ssp. *paratuberculosis* (paraTB), the causative agent of bovine *paratuberculosis*, also known as Johnne's disease, from milk, including colostrum, several aliquots of the milk preparation was spiked with a culture of paraTB to obtain a concentration of 10000 cfu/ml. Then a solution containing methylene blue and crystal violet (double dye solution) and ascorbic 0.001%-1% w/v and the mixtures were incubated with the double dye solution for 10 minutes, 30 minutes, 2 hours, 6 hours and overnight at 4 degrees C. to 50, such as 20-25 degrees C. Each of these incubations was performed together with an uninoculated control, incubated for the same number of hours (negative control 1), an uninoculated control to which dyes was added (negative control 2) and an inoculated control to which no dye was added (positive control).

By the end of the dye incubation period, the milk was immediately tested for the presence of viable paraTB, by culturing a 2-fold dilution row in sterile milk corresponding to 10000, 5000, 2500, 1200, 600, 300 and 150 CFU/ml of untreated milk.

The culturing of paraTB in milk was done according to the non-decontamination protocol published by Giese and Ahrens (2000): The milk was centrifuged (10,000 g for 10 min.) and the cell pellet as well as the cream were resuspended in PBS (using 2 ml PBS for pellet and cream, respectively, from 18 ml milk) and cultured on modified LOwenstein-Jensen medium (Jorgensen, 1982) for ten weeks, identifying paraTB based on colony morphology, slow growth rate, acid-fast staining and the dependence on mycobactin. The whey fraction has previously been shown to contain very few paraTB bacteria in spiked milk. The detection limit of this culture method for para TB in milk is around 100 CFU/ml.

Results are expressed as the titer of paraTB meaning the highest dilution at which paraTB is detectable in either the cream or the pellet fraction.

Defined cultures of paraTB were obtained from the National Veterinary Institute of the Technical University of Denmark.

Example 9

Removal of Dye from Double Dye Disinfected Colostrum

The double dye treatment as described in example 8 was repeated for the dye concentration of 0.1 w/v %.

100 ml colostrum was added 10 ml Double dye stock solution and 5 ml ascorbic acid stock solution. After incubation for 2 hours at room temperature the blue liquid was treated withAmberlite IR-120 (plus)(Sigma-Aldrich co Ltd UK) by mixing with 25 ml adsorbent for 120 minutes. Following incubation the adsorbent was allowed to settle for 30 minutes and the liquid supernatant was collected by decantation.

Visual inspection confirmed that practically all the blue colour had been removed from the colostrum.

REFERENCES

Giese, S. B., Ahrens, P. (2000) Detection of *Mycobacterium avium* subsp. *paratuberculosis* in milk from clinically affected cows by PCR and culture, Vet. Microbiol. 77, 291-297.

Jorgensen, J. B. (1982) An improved medium for culture of *Mycobacterium paratuberculosis* from bovine faeces, Acta. Vet. Scand. 23, 325-335.

The invention claimed is:

1. A method for passively immunising an individual by oral administration of
  a composition comprising immunoglobulins, part or fragments thereof, wherein said immunoglobulins are synthetically multimerised, wherein
    said synthetically multimerised immunoglobulins comprise at least one cross-linking covalent chemical bond between individual immunoglobulins, wherein said immunoglobulin is derived from a starting material selected from the group consisting of milk, colostrum, whey, serum, plasma, and egg, or a part thereof, and wherein said individual is passively immunised by said oral administration.

2. The method according to claim 1, wherein the composition is obtained by a method for producing synthetically multimerised immunoglobulins comprising the steps of:
  i) providing a starting material
  ii) isolating immunoglobulin, part or fragments thereof
  iii) multimerising the isolated immunoglobulin of step ii)
  iv) obtaining multimerised immunoglobulin
    or
  v) providing a starting material
  vi) multimerising components of the starting material of step v)

vii) optionally, isolating immunoglobulin, part or fragments thereof
viii) obtaining multimerised immunoglobulin;
wherein,
said starting material is selected from the group consisting of milk, colostrum, whey, serum, plasma, and egg, or a part thereof.

3. The method according to claim 1 or 2, wherein crosslinking of the immunoglobulins is obtained by use of periodate or a periodate forming compound.

4. The method according to claim 1 or 2, wherein the immunoglobulin is an immunoglobulin fragment.

5. The method according to claim 3, wherein the immunoglobulin is an immunoglobulin fragment.

* * * * *